United States Patent
Ruecroft et al.

(10) Patent No.: US 8,771,744 B2
(45) Date of Patent: Jul. 8, 2014

(54) BARRIER COMPOSITION

(75) Inventors: Graham Ruecroft, Wallingford (GB); Dipesh Parikh, Oxford (GB)

(73) Assignee: Prosonix Limited, Oxford (GB)

( * ) Notice: Subject to any disclaimer, the term of this patent is extended or adjusted under 35 U.S.C. 154(b) by 0 days.

(21) Appl. No.: 13/503,120

(22) PCT Filed: Oct. 20, 2010

(86) PCT No.: PCT/GB2010/051762
§ 371 (c)(1),
(2), (4) Date: May 17, 2012

(87) PCT Pub. No.: WO2011/048412
PCT Pub. Date: Apr. 28, 2011

(65) Prior Publication Data
US 2012/0309729 A1    Dec. 6, 2012

(30) Foreign Application Priority Data

Oct. 21, 2009  (GB) .................................. 0918431.8

(51) Int. Cl.
*A61K 9/14* (2006.01)
*A61K 9/16* (2006.01)
*A61K 9/50* (2006.01)

(52) U.S. Cl.
USPC .......... 424/489; 23/295 R; 514/174; 514/653; 540/71; 564/361

(58) Field of Classification Search
None
See application file for complete search history.

(56) References Cited

U.S. PATENT DOCUMENTS

| 2004/0033266 A1* | 2/2004 | Thassu .......................... 424/489 |
| 2004/0139908 A1 | 7/2004 | Bowe et al. |
| 2004/0258600 A1 | 12/2004 | Josien et al. |
| 2007/0065372 A1 | 3/2007 | Price et al. |
| 2009/0179341 A1* | 7/2009 | McCausland ..................... 264/9 |

FOREIGN PATENT DOCUMENTS

| EP | 0277386 | 8/1988 |
| GB | 2337514 | 11/1999 |
| GB | 2447761 | 9/2008 |
| WO | 2004009057 | 1/2004 |
| WO | 2004064487 | 8/2004 |
| WO | WO 2004064487 A2 * | 8/2004 |
| WO | 2004073827 | 9/2004 |
| WO | 2006090350 | 8/2006 |
| WO | 2010007446 | 1/2010 |
| WO | 2010007447 | 1/2010 |
| WO | 2010007466 | 1/2010 |
| WO | WO 2010007446 A1 * | 1/2010 |

OTHER PUBLICATIONS

G Ruecroft, D Hipkiss, T Ly, N Maxted, PW Cains. "Sonocrystallization: The Use of Ultrasound for Improved Industrial Crystallization." Organic Process Research & Development, vol. 9, 2005, pp. 923-932.*

M Manish, J Harshal, P Anant. "Melt sonocrystallization of ibuprofen: Effect on crystal properties." European Journal of Pharmaceutical Sciences, vol. 25, 2005, pp. 41-48.*

* cited by examiner

*Primary Examiner* — Frederick Krass
*Assistant Examiner* — Isaac Shomer
(74) *Attorney, Agent, or Firm* — Tarolli, Sundheim, Covell & Tummino LLP

(57) ABSTRACT

The invention provides a process for increasing the crystallinity of at least one solid material which is less than 100% crystalline, comprising applying ultrasound to the substantially dry solid material.

14 Claims, 9 Drawing Sheets

Figures

BARRIER COMPOSITION

FIELD OF THE INVENTION

The present invention relates to a process for increasing the level of crystallinity and modifying surface characteristics in an amorphous solid material. The present invention has application in the manufacture of chemicals, such as active ingredient compounds and excipients for use in pharmaceutical formulations, such as inhalation formulations, and in the manufacture of agrochemical formulations, such as liquid-based suspensions.

The present invention is also concerned with the production of active drug particles that are to form a dry powder formulation which is to be administered to the lung, for example using a dry powder inhaler (DPI) device. In particular, the present invention provides the characteristics and preferred processing of particles whereby the performance as such is significantly greater than conventional DPI, pressurized metered-dose inhalers (pMDIs) and nasal suspension powders, in particular DPI and pMDI powders, more particularly DPI powders.

BACKGROUND OF THE INVENTION

Two widely used systems for the administration of drugs to the airways are the dry powder inhalers (DPIs) comprising micronized drug particles as dry powder usually admixed with coarser excipient particles of pharmacologically inert materials such as lactose, and the pressurized metered-dose inhalers (pMDIs) which may comprise a suspension of micronized drug particles in a propellant gas. This present invention is relevant to both these methods of delivery.

Nasal delivery is a means to enable administration of drug particles to the central nervous system (CNS-nose to brain), systemic and topical nasal formulations whether as powders or of liquid suspension. Various breath activated devices deliver intranasal drugs to targeted regions of the nasal cavity, including the sinuses and the olfactory region, without lung deposition. This present invention is relevant to this method of delivery.

The control of crystal and precipitate particle size of active and other compositional ingredients is necessary in industries in which the final product form of the active ingredient of interest is in the form of a fine powder, such as in the pharmaceutical and agrochemical industries. The manner in which an active ingredient behaves in a biological system depends upon many factors inter alia the size of the particle and the crystal form. Small particles may be made by processes such as milling, but such processes may have a detrimental effect on the material properties of the milled particles. Furthermore, a significant proportion of particles may be produced which are of a shape that is unsuitable for a given end use. When particles are milled they may undergo morphological alterations, leading to undesirable surface polymorphological transformation which in turn may give rise to the formation of amorphous structures that are unsuitable for end purpose applications, such as in a pharmaceutical formulation designed for inhalation. In addition, milling generates considerable heat which may make particulate milling inappropriate, for example, where the active ingredient is a low melting solid. In addition, the physical performance of particles destined for use in aerosols may be compromised if they become highly charged as a result of milling.

Techniques for the production of drug particles may include the generation of an aerosol of droplets from a solution of the drug and subsequent spray drying of the droplets to solidify the particles. Spray drying is one of the most widely used of industrial processes involving particle formation and drying. It is highly suited for the continuous production of dry solids in either powder, granulate or agglomerate form from, for example, liquid feed stocks as solutions, emulsions or pumpable suspensions. Therefore, spray drying is an ideal process where the end-product should comply with quality standards regarding such parameters as particle size distribution, residual moisture content, bulk density, particle shape and the like. A disadvantage of conventional spray drying techniques is that the particles being dried tend to be in an amorphous form, perhaps as high as 100%, rather than in a crystalline particulate form, since solidification is typically rapid, and in addition the processing leads to a high degree of agglomeration of dried particulates. Freeze drying of aerosol droplets is also used in the art to obtain particles but again, the typically rapid solidification that occurs generally leads to the generation of amorphous particles.

WO 2004/073827 describes the preparation of particles in a process referred to as SAX, comprising the steps of forming a solution of a desired substance in a suitable solvent, generating an aerosol therefrom, collecting the aerosol droplets in a non-solvent for the said substance, and applying ultrasound to the droplets dispersed in the non-solvent to effect crystallisation of the substance. A disadvantage of this technique is the need to have a critical control over the degree of solvent evaporation from the aerosol.

Inhalation represents a very attractive, rapid and patient-friendly route for the delivery of systemically acting drugs, as well as for drugs that are designed to act locally on the lungs themselves, such as asthma, chronic obstructive pulmonary disease and infection. It is particularly desirable and advantageous to develop technologies for delivering drugs to the lungs in a predictable and reproducible manner. Drug inhalation benefits include rapid speed of onset; improved patient acceptance and compliance for a non-invasive systemic route; reduction of side effects; product life cycle extension; improved consistency of delivery; access to new forms of therapy, including higher doses, greater efficiency and accuracy of targeting.

Dry powder inhalation (DPI) plays an important role in the treatment of diseases of the lung. Primarily they were developed to overcome problems encountered using Metered Dose Inhalers (MDIs), and later, because they are propellant free and hence more environmental friendly. Using an MDI the patient has to coordinate inhalation and inhaler actuation so that the aerosol cloud can reach the lungs. Dry Powder inhalers (DPIs) are breath actuated, so that theoretically the aerosol cloud should reach the lungs without problems. However, problems arise due to technical limitations with respect to handling, content uniformity of dose and control of dose. Also, the inspiratory flow rate varies between patients and depends on the mechanical principle of the DPI. DPIs which reduce the inspiratory flow rate considerably due to a high flow resistance are less suitable, because the rate of lung deposition of an aerosol cloud depends on the inspiratory flow rate.

Powder technology, however, for successful dry powders and DPI products remains a significant technical hurdle. Formulations must have suitable flow properties, not only to assist in the manufacture and metering of the powders, but also to provide reliable and predictable resuspension and fluidisation, and to avoid excessive retention of the powder within the dispensing device. The drug particles or particles of pharmaceutically active material (also referred to herein as API particles) in the resuspended powder must aerosolise appropriately so that they can be transported to the appropriate target area within the lung. Typically, for lung deposition, the active particles have a diameter of less than 10 µm, frequently 0.1 to 7 µm or 0.1 to 5 µm.

In this kind of system the interaction between drug-to-drug and drug-to-carrier particles and particle-to-wall are of great importance for successful drug delivery to the deep lung. The interaction between particles is determined by adhesion forces such as van der Waals, capillary, and coulombic forces. The strength of these forces is affected by the particle size, shape, and morphology. Spherical or rounded particles with a rough surface are considered best for pulmonary drug delivery due to their small contact area and increased separation distance between particles. Large separation distance decreases the attachment forces and improves the powder dispersion. Particle engineering for the optimum drug particles together with DPI device engineering are essential for efficient drug delivery via the lungs. WO 2006056812 reports the invention concerned with a refinement of the processing of particles that are to form a dry powder formulation which is to be administered to the lung using a dry powder inhaler (DPI) device whereby the processing of particles of active material and particles of carrier material is carried out in the presence of additive material to provide a powder composition which exhibits excellent powder properties.

When dry powders are produced in conventional processes, the active particles will vary in size, and often this variation can be considerable. This can make it difficult to ensure that a high enough proportion of the active particles are of the appropriate size for administration to the correct site. It is therefore desirable to have a dry powder formulation wherein the size distribution of the active particles is as narrow as possible. For example, preferably the particle distribution is Gaussian, preferably the particle distribution is monomodal. Further, for example, the geometric standard deviation of the active particle aerodynamic or volumetric size distribution is preferably not more than 2, more preferably not more than 1.8, not more than 1.6, not more than 1.5, not more than 1.4, or even not more than 1.2. This will improve dose efficiency and reproducibility.

The Mass Median Aerodynamic Diameter (MMAD) is the particle diameter below which 50% of the particles enter an impactor suitable for determining in vitro performance of inhaled drug particles and takes account of both shape and density. A sample with a MMAD of (say) 5 µm will have 50 per cent of the total mass (i.e. not the total number) of particles with a diameter of more than 5 µm and 50 per cent with a diameter of less than 5 µm.

Fine particles, with an MMAD of less than 10 µm and smaller, tend to be increasingly thermodynamically unstable as their surface area to volume ratio increases, which provides an increasing surface free energy with this decreasing particle size, and consequently increases the tendency of particles to agglomerate and the strength of the agglomerate. In the inhaler, agglomeration of fine particles and adherence of such particles to the walls of the inhaler are problems that result in the fine particles leaving the inhaler as large, stable agglomerates, or being unable to leave the inhaler and remaining adhered to the interior of the inhaler, or even clogging or blocking the inhaler.

The uncertainty as to the extent of formation of stable agglomerates of the particles between each actuation of the inhaler, and also between different inhalers and different batches of particles, leads to poor dose reproducibility. Furthermore, the formation of agglomerates means that the MMAD of the active particles can be vastly increased, with agglomerates of the active particles not reaching the required part of the lung. These µm to sub µm particle sizes required for deep lung or systemic delivery lead to the problem that the respirable active particles tend to be highly cohesive, which means they generally exhibit poor flowability and poor aerosolisation.

To overcome the highly cohesive nature of such respirable active particles, formulators have, in the past, included larger carrier particles of an inert excipient in powder formulations, in order to aid both flowability and drug aerosolisation. These large carrier particles have a beneficial effect on the powder formulations because, rather than sticking to one another, the fine active particles tend to adhere to the surfaces of the larger carrier particles whilst in the inhaler device. The active particles are released from the carrier particle surfaces and become dispersed upon actuation of the dispensing device, to give a fine suspension which may be inhaled into the respiratory tract.

Whilst the addition of relatively large carrier particles does tend to improve the powder properties, it also has the effect of diluting the drug, usually to such an extent that 95% or more by total weight of the formulation is carrier. Relatively large amounts of carrier are required in order to have the desired effect on the powder properties because the majority of the fine or ultra-fine active particles need to adhere to the surfaces of the carrier particles, otherwise the cohesive nature of the active particles still dominates the powder and results in poor flowability. The surface area of the carrier particles available for the fine particles to adhere to decreases with increasing diameter of the carrier particles. However, the flow properties tend to become worse with decreasing diameter. Hence, there is a need to find a suitable balance in order to obtain a satisfactory carrier powder. An additional consideration is that one can get segregation if too few carrier particles are included, which is extremely undesirable.

An additional problem experienced by formulators is the variability in surface properties of drug and excipient particles. Each active agent powder has its own unique inherent stickiness or surface energy, which can range tremendously from compound to compound. Further, the nature of the surface energies can change for a given compound depending upon how it is processed. For example, jet milling is notorious for generating significant variations in surface properties because of the aggressive nature of the collisions it employs. Such variations can lead to increased surface energy and increased cohesiveness and adhesiveness. Even in highly regular, crystalline powders, the short range Lifshitz-van der Weals forces can lead to highly cohesive and adhesive powders.

If no carrier excipient is used, the micronized drug particles are loosely agglomerated via Lifshitz-van der Weals forces only. It is important for the function of such a formulation that no capillary forces are formed, because the particle agglomerates must be de-agglomerated in the air stream. Capillary forces are usually several times larger than, for example, Lifshitz-van der Weals forces, and the ability of such an agglomerate to be split into the single particles decreases with increasing autoadhesion forces holding the agglomerates together. Such a loose agglomeration can be achieved using a spheronisation process.

The forces acting on a particle adhered to a carrier particle when placed into an air stream can be described by lift force (the lift of smaller particle away from carrier particle; this can be neglected for micronized powders), the drag force (to compensate for adhesion and friction forces), the adhesion force and friction force (force preventing tangential displacement of two surfaces in contact). These last two hinder the detachment of the drug particles from the carrier surface. The success or failure of an interactive powder mixture as dry powder inhalation depends mainly on the magnitude of the adhesion forces, which fix the drug particles onto the carrier surface.

Obviously, a very high adhesion force is unwanted, because if the drug-carrier units cannot be split into their single components by the drag force, the whole drug-carrier units are swallowed. A balanced adhesion force promotes the split of the drug-carrier units into the micronized drug particles, which are inhaled, and the coarse carrier particles, which are swallowed. On the other hand, a too small adhesion force between drug and carrier particles might result in particle segregation and hence in higher variability in the content uniformity of dose. Also, drug particles are easier removed from the carrier particles during the sliding contact with the inhaler device walls, to which they tend to adhere firmly. Therefore, more drug is lost in the inhaler device.

The prior art teaches that the adhesion force in interactive powder mixtures for inhalation can be manipulated in several ways. First, the carrier particles can be chosen according to their median particle size, shape and surface roughness, which will result in large differences in the adhesion force for a defined mixing procedure and consequently in different aerosolisation properties.

A decrease in median particle size increases the adhesion force between drug and carrier particles. Larger adhesion forces are also found for irregular shaped or elongated carrier particles. This effect can be explained by an increase in friction during mixing. Surface roughness will either increase or decrease the adhesion force depending on the magnitude of the roughness. An increase in adhesion force will be found for extremely smooth carrier particle surfaces due to an increase in the true area of contact, or for very rough carrier particle surfaces, because here the wider spacing between the asperities allows mechanical entrapment of the micronized drug particles.

In typical DPI formulation, powders are pre-blended, which results in autoadhesion between the finer and coarse carrier particles. The finer carrier particles auto adhere, mainly due to mechanical entrapment in the grooves and clefts of the coarse carrier particle surfaces. The amount of finer carrier particles is thus physically removed, and the flow properties of the carrier powder are improved. Corrasion (a geological term implying filling of valleys) leads to a less wavy carrier particle surface, so that micronized drug particles are less likely to be mechanically trapped or embedded in the carrier particle surface. Corrasion also increases the micro-roughness of the carrier particle surfaces and hence reduces the adhesion force between drug and carrier particles due to a reduced true area of contact. However, it has been found that with respect to the adhesion forces and hence the dry powder inhalation function, corrasion is not always of advantage. A minimum surface roughness of the coarse carrier particles is required to allow the embedment of the finer carrier particles in the sense of corrasion. If the coarse carrier particle surface is relatively smooth, the finer carrier particles autoadhere in such a way, that the apparent macro-roughness of the carrier particle surface is increased, which in return offers more sites for the drug particles to be mechanically trapped. In this case, the drug particles can be removed from the carrier particle surfaces only as agglomerates with the finer carrier particles during re-suspension, and the drug deposition in the lungs depends on the size of these agglomerates.

The choice of the carrier material definitely influences the strength of the adhesion forces between drug and carrier particles. However, the place of application i.e. inhalation into the lungs limits this choice dramatically. To date, only lactose monohydrate and glucose are used as carrier materials in commercial dry powder inhalations. Glucose adsorbs moisture rapidly if stored in an environment of more than 55% relative humidity of the storage air. This will lead to strong capillary forces between drug and carrier particles. Lactose monohydrate has been claimed to reduce the vulnerability of the drug-carrier units to increased levels of humidity. However, adhesion force measurements between micronized drug and lactose monohydrate carrier particles after storage under different humidity conditions cast doubts on this opinion.

The use of an interactive powder mixture eases the handling of very low dose drugs for inhalations (for example salmeterol xinafoate: 50 microgram), so that they can be provided in single dose units such as foil blisters (such as in Advair Discus inhaler device) or capsules. Also, the increased homogeneity and reduced segregation of such mixtures is an advantage for the content.

Two common techniques to produce fine particles for DPIs are mechanical micronization and spray drying. A high-energy milling operation generates particles that are highly charged and thus very cohesive. To decrease cohesiveness, surfactants are used, for example, in wet milling. The milling process also introduces surface and crystallographic damage that affects powder stability.

The produced particles often contain irregular fragments that can form strong aggregates. In addition, multistep processing may cause significant losses of materials during powder production and variability of the product properties from batch to batch. Unlike milling, the spray-drying technique is a one-step continuous process that can directly produce pharmaceutical particles with a desired size. No surfactants or other solubilizing agents are needed in the process. However, the thermal history and drying rate of each particle is difficult to control due to the high flow rates needed in the process and limited controllable parameters. Consequently, the produced particles are usually amorphous and thus sensitive to temperature and humidity variations that may cause structural changes and sintering of the particles during storage of the powder.

SUMMARY OF THE INVENTION

According to a first aspect of the invention there is provided a process for increasing the crystallinity of at least one solid material which is less than 100% crystalline, comprising applying ultrasound to the substantially dry solid material.

According to a second aspect of the invention, there are provided particles comprising at least one substance obtainable by the process as described herein. There are also provided formulations having particles comprising at least one particulate substance obtainable by the process as described herein.

Such particles and formulations containing them are particularly useful in producing inhalable medicament formulations. Such particles and formulations comprising such particles exhibit surprising in vitro performance compared with conventionally prepared particles. This significant performance increase is quantified by proportional increase in Fine Particle Fraction (FPF, the % relative to the delivered dose, defined as the sum of all stages of an impinger and the throat). These particles have excellent performance characteristics for drug formulation in DPI. These particles also exhibit surprising in vivo performance compared with conventional particles, with respect to rate of dissolution and FPF delivered to the lungs.

Hereinafter, a solvent in which the solid material is insoluble or poorly soluble shall be referred to as a non-solvent. As used herein, a non-solvent is one in which the solid material is soluble in an amount of less than 0.1 mg per ml at 25° C., preferably less than 0.05 mg per ml at 25° C., preferably less than 0.01 mg per ml at 25° C.

Conversely, as used herein, a solvent is one in which the solid material is soluble in an amount of greater than 0.1 mg per ml at 25° C., preferably greater than 0.5 mg per ml at 25° C., preferably greater than 1 mg per ml at 25° C., preferably greater than 5 mg per ml at 25° C., preferably greater than 10 mg per ml at 25° C.

Preferably, the solid material utilised in the present invention is a particulate solid material. The particles preferably have a MMAD of up to about 10 µm, preferably from about 100 nm to about 10 µm, preferably from about 100 nm to about 5 µm and most preferably from about 100 nm to about 2 µm, for example, about 110 nm, about 250 nm, about 400 nm, about 700 nm or about 1 µm, and the like.

The aerodynamic diameter is the diameter of a sphere of unit density which behaves aerodynamically as the particle of the test substance. It is used to compare particles of different sizes, shapes and densities and to predict where in the respiratory tract such particles may be deposited. The term is used in contrast to volume equivalent, optical, measured or geometric diameters which are representations of actual diameters which in themselves cannot be related to deposition within the respiratory tract.

A number of methods are available to determine the size distribution of respirable particles and (to a lesser extent) the distribution of inhalable particles; for an indication of the particle size the Mass Median Aerodynamic Diameter (MMAD) and Geometric Standard Deviation (GSD) can be calculated. The MMAD is a statistically derived figure for a particle sample: for instance, an MMAD of 5 µm means that 50% of the total sample mass will be present in particles having aerodynamic diameters less than 5 µm, and that 50% of the total sample mass will be present in particles having an aerodynamic diameter larger than 5 µm.

Cascade impactors such as the Anderson Cascade Impactor or Next Generation impactor, preferably Next Generation Impactor, can be used to obtain the size distribution of an aerosol (or a dust cloud). Air samples are withdrawn through a device, which consists of several stages on which particles are deposited on e.g. glass or glass fibre. Particles will impact on a certain stage depending on their size. The cut-off size can be calculated from the jet velocities at each stage by weighing each stage before and after sampling and the MMAD derived from these calculations. Despite the limitations in this method, namely particles bouncing off, overloading and fluctuation in flow rate etc, it is a well established technique to measure the airborne size distribution of an aerosol and it's MMAD.

The particle size can be measured by laser diffraction techniques: Light from a laser is shone into a cloud of particles, which are suspended in a transparent gas such as air. The particles scatter the light; smaller particles scattering the light at larger angles than bigger particles. The scattered light can be measured by a series of photodetectors placed at different angles. This is known as the diffraction pattern for the sample. The diffraction pattern can be used to measure the size of the particles using well documented light scattering theory. The particles are assumed to be spherical but few particles are actually spherical. The particle diameters are calculated from the measured volume of the particle, but assume a sphere of equivalent volume.

Preferably, the solid material utilised in the present invention is obtained from a process selected from the group consisting of mechanical micronization, milling, jet milling, grinding, rapid precipitation, freeze drying, lyophilisation, rapid expansion of supercritical solutions, spray drying or mixtures thereof. Most preferably, the solid material utilised in the present invention is obtained by a process of spray drying. Conventional spray drying techniques may be used.

Preferably, prior to the application of one of the above processes, the solid material is substantially amorphous, for example, less than 50% crystalline, more preferably less than 40% crystalline, more preferably less than 25% crystalline, more preferably less than 10% crystalline, more preferably less than 5% crystalline, for example less than 1% crystalline.

When the solid material utilised in the present invention is obtained from mechanical micronization, milling, jet milling, grinding or mixtures thereof, the solid material prior to one of these processes may be substantially crystalline, such as more than 50% crystalline, for example more than 60% crystalline, for example more than 75% crystalline, for example more than 90% crystalline, for example more than 95% crystalline, for example more than 99% crystalline. After one of the four processes, or mixtures thereof, the solid material may be substantially crystalline at the core of the particle, and substantially amorphous on the outer layer of the particle.

A number of techniques may be used to determine crystalline content. For example, PXRD (Powder X-ray Diffraction) is a technique for looking at X-ray Diffraction patterns in solid materials. Crystalline particles have distinct 'fingerprint' patterns for a given polymorph. Conversely amorphous compounds show little or no diagnostic patterns and show up simply as a broad hump or noise. Differential Scanning Calorimetry (DSC) also reveals a clean melting point and measurement of heat of fusion which can equate to level of crystallinity in a given sample. Amorphous materials show inconsistent behaviour in the DSC profile. DSC of crystalline materials illustrates a sharp endotherm indicating crystalline nature. Dynamic Vapor Sorption (DVS) provides a rapid and continuous method for measuring the isotherm and moisture uptake behaviour of crystalline and amorphous materials. In conjunction with DSC it can be used to measure the stability of products. Finally Raman analysis can give an indication of crystalline material and indeed distinguish between different polymorphs. Amorphous materials do not have the same diagnostic patterns and so are distinguishable from crystalline phases. For the purposes of the present application, Differential Scanning Calorimetry (DSC) is the preferred method of measurement of crystallinity. DSC experiments can be performed with a number of commercial apparatus including TA Instruments' DSC Q2000 V24.2 build 107, the latter being the preferred instrument for measuring DCS according to the present invention. Typically an accurate amount of material is charged to the sample pan of the DSC instrument and subjected to a heating ramp of up to 100° C./min to around 275° C. The melting point endotherm and integral of the heat flow, as a measure of heat of fusion, is a qualitative and quantitative measurement respectively of crystallinity. In particular, for a given solid material, DSC provides a direct comparison of two samples thereof and clearly shows whether one is more or less crystalline than the other.

Furthermore thermogravimetric analysis (TGA) is a simple analytical technique that measures the weight loss (or weight gain) of a material as a function of temperature. As materials are heated, they can lose weight from a simple process such as drying, or from chemical reactions that liberate gasses. Some materials can gain weight by reacting with the atmosphere in the testing environment. Since weight loss and gain are disruptive processes to the sample material or batch, knowledge of the magnitude and temperature range of those reactions are necessary in order to design adequate thermal ramps and holds during those critical reaction periods. A sample of the test material is placed into a high alumina cup that is supported on, or suspended from an analytical balance located outside the furnace chamber. The balance is zeroed, and the sample cup is heated according to a predetermined thermal cycle. The balance sends the weight signal to the computer for storage, along with the sample temperature and the elapsed time. The TGA curve plots the TGA signal, converted to percent weight change on the Y-axis against the reference material temperature on the X-axis. With respect to the current invention TGA is used to measure the loss of solvent or water from an amorphous or crystalline sample as a function of temperature. Non-solvated or non-hydrated crystalline samples will tend to show some stability and zero or minimal mass loss with temperature, but may show loss if undergoing gross chemical thermal decomposition.

Additionally or alternatively, prior to the application of the present process, the solid material may comprise a metastable crystalline material.

For any particular material, the skilled person can readily determine whether a solid material is insoluble or poorly soluble therein. For example, High Performance Liquid Chromatography (HPLC) or Gas Liquid Chromatography (GLC) allow one to determine the level of solubilised substance in a liquid sample when it is saturated, by analysis of clear samples, making reference against solutions of known concentration. The former method is more typically used for pharmaceutical products whereas the latter is used when the material being analysed is sufficiently volatile to be vaporised at temperatures up to 300° C. which precludes most pharmaceutical products. Preferably, water is used as the non-solvent for poorly water soluble materials. For water soluble materials, preferably non-solvent hydrocarbons are used, for example, heptane. Further non-solvents for water soluble materials may include ethers (methyl tert-buty ether), alcohols (ethanol) and ketones (butanone) as appropriate.

The ultrasound is preferably applied for a suitable period of time and temperature required to convert at least a portion of the amorphous material into crystalline material, or to convert a metastable material into a more stable material. For example, the process, that is the application of the ultrasound, is preferably carried out for a period of greater than 0.1 ms, more preferably greater than 1 ms, more preferably greater than 1 minute, for example, between 1 second and 24 hours, more preferably between 1 minute and 6 hours, more preferably between 5 minutes and 1 hour.

The technique can be carried out with ultrasound in the presence of elevated temperature. The elevation of temperature may be useful when, for example, the sample has to be heated to above its glass transition point. In addition, the thermal energy can be beneficial and complementary to the applied ultrasonic energy in speeding up the rate of conversion that would be otherwise observed at ambient temperature.

Preferably the solid material used in the present invention is substantially free of solvent. By substantially free of solvent it is meant that the solid material contains less than 2% by weight of liquid, more preferably less than 1%, more preferably less than 0.5%, more preferably less than 0.1% by weight of solvent.

Preferably, the solid material used in the present invention is dry. This means that it is preferably substantially free from liquid, including solvents, non-solvents, water and organic solvents. This means that the solid material is substantially free of free water or free solvent. By substantially free from liquid it is meant that the solid material contains less than 5% by weight of liquid, more preferably less than 4%, more preferably less than 3%, more preferably less than 2%, more preferably less than 1%, more preferably less than 0.5%, more preferably less than 0.1% by weight of liquid.

Preferably, the substantially dry solid material does not comprise any non-solvent.

Solid materials containing water of hydration, and molecular solvates can be substantially free from liquids and solvents since they contain only the prerequisite amount of water or solvent necessary for incorporation into the unit cell of the crystal. Otherwise they are essentially free of free water or solvent.

The process of the present invention finds particular utility in the processing of spray dried particles, comprising a substance selected from the group consisting of an active pharmaceutical ingredient, an active agrochemical ingredient, a pharmaceutical excipient, an agrochemical excipient and appropriate mixtures of two or more thereof. By "appropriate", it is meant that active pharmaceutical ingredient may be combined with other active pharmaceutical ingredient and/or pharmaceutical excipient(s), but one would not normally combine a pharmaceutical active ingredient with an agrochemical excipient for example.

Highly disordered amorphous materials have lower energy barriers to overcome in order to be dissolved into solution compared with highly ordered crystalline structures with significant lattice energies. This ease of solubilisation can be an attractive property given that many new drug substances in stable crystalline form are extremely insoluble in water. The highly disordered molecular state required can be made via high energy processes such as milling, lyophilisation and spray drying. However this structure requires a degree of stabilization before it can be rendered suitable for a structured drug product and instability can be suppressed over its lifetime from manufacture to patient.

The physicochemical instability of amorphous pharmaceutical materials is the major factor precluding their widespread use. Such solids are often highly reactive to mechanical and thermal stress above their glass transition temperature (Tg); a critical parameter in defining chemical and physical stability, and viscoelastic properties. Above the Tg the amorphous material can be characterized by increased molecular motion, in turn giving rise to plasticity and viscoelasticity. Below Tg amorphous materials can be very rigid and brittle structures with very low molecular freedom within the construct. Tg can be determined by calorimetric, thermochemical, volumetric and spectroscopic measurements. Despite the abundance of methods the determination of Tg for pharmaceutical solids can be difficult. The Tg of a solid may be determined by Differential Scanning Calorimetry using a heating and cooling rate of around 20 k/minute. The range of Tg values for dry drugs is −100 to +250° C. Whilst many pharmaceutical materials have Tg values above normal operating temperatures the plasticising effects of residual solvents, absorbed water and other additives or impurities are not easily quantified. The presence of such impurities will in effect lower the Tg and hence render the particle or material more plastic. Water is known to cause such plasticising effects. Importantly whilst it is often assumed that amorphous materials are inherently stable below Tg, there is evidence that destabilisation can occur in the glass state. This invention takes advantage of the instability of amorphous materials whether in the glassy state or preferably in a condition above the respective Tg, and implied from this is that the solid material would be in a highly plastic or viscoelastic state. In order to reach this state this invention also takes advantage of the plasticising effects of residual water of other plasticising solvent impurities.

Mixtures of amorphous materials exhibit a single Tg intermediate between the Tg values for each component. One (minor) component may lower the Tg of the other (major) component and bestow more plastic-like properties on the major component. For example water has a Tg at 135 K and acts as a potent plasticiser for other materials. It is known that unstable amorphous pharmaceutical materials readily absorb water from the atmosphere which then undergo collapse of the structure to leave a viscous glue-like material or alternatively the material may crystallize.

While not wishing to be limited by theory, it is believed that the residual solvent in the substantially dry solid material, reduces the Tg of the substantially dry solid material. The effect of this is to cause the substantially dry solid material to increase its crystallinity when ultrasound is supplied. This can be attributed to the ultrasonic energy improving the kinetics of crystal nucleation within the unstable and mechanical stress susceptible plasticized amorphous material. Vibration effects and inter-particle collision may also be responsible.

The present invention can be carried out with ultrasound in the presence of elevated temperature. The elevation of temperature may be useful when, for example, the sample has to be heated to above its glass transition point. In addition, the thermal energy can be beneficial and complementary to the applied ultrasonic energy in speeding up the rate of conversion that would be otherwise observed at ambient temperature. The elevation of temperature may be achieved by the application of warm or hot gas, by way of a thermal oven or by way of application of microwaves. Microwave energy can be applied concurrently with the ultrasound energy. Microwaves relate to electromagnetic waves lying between infrared and radio frequencies and correspond to wavelengths of 1 centimeter to 1 meter, or frequencies of 30 GHz to 300 MHz respectively. More specifically, in relation to the present invention wavelengths of 12.2 centimeter to 33.3 centimeter, or frequencies of 2.45 GHz to 900 MHz respectively, can be used.

In a preferred embodiment of the present invention, there is provided a process for increasing the crystallinity of at least one solid material which is less than 100% crystalline which comprises:
 i) forming a solution of at least one solid material in a solvent;
 ii) subjecting the solution to a process selected from the group consisting of rapid precipitation, freeze drying, lyophilisation, rapid expansion of supercritical solutions, spray drying or mixtures thereof, wherein the said dissolved solid material is converted into a substantially dry solid material; and
 iii) applying ultrasound to said substantially dry solid material from step (ii).

In such a process, step (ii) preferably comprises spray drying of the solution of the solid material. Conventional spray drying may be used. In the spray drying process, the solid material produced is usually substantially amorphous.

Preferably, after the application of step (ii), the material going into step (iii) is substantially amorphous, for example, less than 50% crystalline, more preferably less than 40% crystalline, more preferably less than 25% crystalline, more preferably less than 10% crystalline, more preferably less than 5% crystalline, for example less than 1% crystalline.

Optionally, step (iii) further comprises applying microwave energy to said substantially dry solid material from step (ii). The microwave energy may be applied before, during or after the application of the ultrasound.

In step (iii) the term "applying" means exposing the dry solid material to the effects of ultrasound in a resonating chamber, sieve, conveyor or the like. This may take place in the same or a separate vessel, container or device to the one used to collect the material produced by step (ii). Step (iii), is carried out in a suitable chamber or device without the need for a liquid medium to transmit the ultrasound.

Preferably in step (iii) the dry solid material is in a device capable of handling dry powders and the ultrasound and optionally microwave energy is applied to the dry solid material when in contact with resonating surfaces within said device.

Preferably, the solid material produced by step (ii) is substantially dry. This means that preferably all of (100%) of the solid material entering process step (iii) is preferably substantially free from solvent, including water and organic solvents (wherein the term "substantially free from solvent" is defined above).

Preferably step (iii) is carried in the presence of air, more preferably in the presence of inert gases such as helium, argon, nitrogen or combinations thereof.

For any given solid material, the skilled person is capable of determining suitable solvents therefor, without burden. Some examples of solvent suitable for certain solid materials are as follows. Volatile organic solvents such as methanol, ethanol, dichloromethane, ethyl acetate, acetone, 2-propanol and non-organic solvents such as water would be typical solvents for pharmaceutically active ingredients.

Preferred excipients may include, for example, lactose and stearic acid. Lactose may be dissolved in water or ethanol/water mixture. Stearic acid may be dissolved in ethyl acetate or ethanol.

Whilst not an exhaustive list, some examples of solvents are methanol, ethanol, acetone, ethyl acetate and dichloromethane.

The concentration of the solid material (which is preferably a pharmaceutically acceptable substance, a pharmaceutically acceptable excipient or a mixture thereof) in the solution formed in step (i) of the process is preferably from 10 mg/ml to 800 mg/ml, more preferably in the range of 50 mg/ml to 600 mg/ml, more preferably 100 mg/ml to 400 mg/ml.

Preferably, the above process is sequential, and step (iii) take place immediately after step (ii). By "immediately after", it is preferably meant that the spray dried particles of step (ii) are processed in step (iii) within 1 hour of undergoing step (ii), preferably within 30 minutes, preferably within 5 minutes, preferably within 1 minute of undergoing step (ii). Preferably, "immediately" means without any intermediate steps. Preferably, the above process is a continuous process. For example the process can be continuously fed with unprocessed material, and the processed material can be continuously or incrementally removed. Alternatively, the process may be a batch-type process wherein the process is fed batchwise with unprocessed material, and the processed material can be removed in batches.

Alternatively, step (ii) can be carried out prior to step (iii), such as about 6 months prior, more preferably about 3 months prior, more preferably about 1 month prior, more preferably about 1 week prior, more preferably about 1 day prior to step (iii).

The resultant solid material from step (iii) may hereinafter be referred to as "active particles".

In a further embodiment of the present invention, there is provided a process for increasing the crystallinity of at least one solid material which is less than 100% crystalline which comprises:
(a) subjecting at least one solid material to mechanical micronization, milling, jet milling, grinding or mixtures thereof; and
(b) applying ultrasound to the solid material from step (a).

Optionally, step (b) further comprises applying microwave energy to said solid material from step (a). The microwave energy may be applied before, during or after the application of the ultrasound.

After the application of step (a), the material going into step (b) is for example more than 50% crystalline, for example more than 60% crystalline, for example more than 75% crystalline, for example more than 90% crystalline, for example more than 95% crystalline, for example more than 99% crystalline, or for example, less than 50% crystalline, for example less than 40% crystalline, for example less than 25% crystalline, for example less than 10% crystalline, for example less than 5% crystalline, for example less than 1% crystalline.

In step (b), the term "applying" means exposing the dry solid material to the effects of ultrasound in a resonating chamber, sieve, conveyor or the like. This may take place in the same or a separate vessel, container or device to the one used to collect the material produced by step (a). Step (b) is carried out in a suitable chamber or device without the need for a liquid medium to transmit the ultrasound and optional microwave energy.

In addition to any agitation which may be effected on the particles by the application of ultrasound, further agitation may be applied in the form of mixing, aerating, shaking, rolling, spinning or the like, or mixtures of these techniques. This may be used to move the particles about, thereby exposing them to the ultrasound and/or averaging their exposure to the ultrasound.

Preferably in step (b) the dry solid material is in a device capable of handling dry powders and the ultrasound is applied to the dry solid material when in contact with resonating surfaces with in said device. Step (b) may occur immediately after step (a) where "immediately after" is as defined above. Alternatively, step (a) can be carried out prior to step (b), such as about 6 months prior, preferably about 3 months prior, more preferably about 1 month prior, more preferably about 1 week prior to step (b).

For formulations to reach the deep lung or the blood stream via inhalation, the active agent in the formulation must be in the form of very fine particles, for example, having a mass median aerodynamic diameter (MMAD) of less than 10 µm. It is well established that particles having an MMAD of greater than 10 µm are likely to impact on the walls of the throat and generally do not reach the lung. Particles having an MMAD in the region of 5 to 2 µm will generally be deposited in the respiratory bronchioles whereas particles having an MMAD in the range of 3 to 0.05 µm are likely to be deposited in the alveoli and to be absorbed into the bloodstream.

Ideally the active particles in a dry powder formulation should have an MMAD of not more than 10 µm, preferably not more than 5 µm, more preferably not more than 3 µm, more preferably not more than 2.5 µm, more preferably not more than 2.0 µm, more preferably not more than 1.5 µm, or preferably not more than 1.0 µm.

Of major importance is the composition of a dry powder inhalation. In a dry powder inhaler (DPI), a mixture of active particles (1-5 µm) and coarse carrier particles such as lactose (50-500 µm) may be used to obtain an effective drug particle discharge.

The spray dried particles preferably have a MMAD of up to about 10 µm, preferably from 100 nm to 10 µm, preferably from about 100 nm to about 5 µm and most preferably from 100 nm to about 2 µm, for example, about 110 nm, about 250 nm, about 400 nm, about 700 nm, about 1 µm, and the like.

The final product of the process, the active particles, may also have a MMAD of up to about 10 µm, preferably from 100 nm to 10 µm, preferably from about 100 nm to about 5 µm and most preferably from 100 nm to about 2 µm, for example, about 110 nm, about 250 nm, about 400 nm, about 700 nm, about 1 µm, and the like.

The frequency of the ultrasound waves used in the process of the present invention is preferably in the range of from 16 kHz to 1 MHz, preferably from 10-500 kHz, more preferably from 10-100 kHz such as at 10, at 20, 40, 60, 80, or 100 kHz or at any frequency therebetween.

The frequency of the microwaves energy used in the process of the present invention is preferably in the range of from 30 GHz to 300 MHz, more preferably from 2.45 GHz to 900 MHz.

In addition to increasing the crystallinity of the solid material produced by the process of the present invention, the application of the ultrasound may also be used to reduce the amount of agglomerated particulate material. This agglomeration reduction preferably takes place at the same time as step (iii) or (b) referred to above.

Depending on the kind of amorphous, partially amorphous, or metastable crystalline form of the substantially dry solid material that is subjected to ultrasonic irradiation, the particle may be transformed into a smaller and/or more stable form of itself. For example, an active ingredient may be transformed into a more stable crystalline form or, should the particle prior to ultrasonic irradiation be of a material that is present in an unstable amorphous form, it may be transformed into a more stable amorphous form. Whatever form the particle has prior to application of ultrasonic irradiation, on application of ultrasonic irradiation as outlined herein, the particle properties are altered, resulting in the formation of more stable particles which may be used in a pharmaceutical or other application, such as an agrochemical application, in a more efficient manner. Preferably, the particles obtained from the process are highly crystalline and stable.

Once the ultrasonic irradiation step has been applied, the crystals can be collected directly into suitable storage containers such as polyethylene bags or polypropylene or glass jars.

By manipulating the spray drying conditions and ultrasonic and optional microwave treatment regime in the process of the present invention the inventors have now made it possible to provide crystals or amorphous bodies having predetermined characteristics. By treating a spray dried material with ultrasound and optionally microwave energy for a predetermined period of time and temperature, certain characteristics may be reproducibly obtained. These characteristics may include particle morphology, surface free energy, particle size distribution, desired polymorph, and in terms of isolated particles flowability, reduced electrostatic and cohesive/adhesive properties.

The solid material, preferably particulate solid material that is subject to the process of the invention is preferably an active ingredient or a desired precursor thereof, such as a drug or pro-drug or an agrochemical of interest that is able to form crystals or undergo alterations in morphology that results in a more stable form of the particle. Typically, such modified particles possess physical properties that make them more amenable for use in a desired context, such as in conventional drug delivery vehicles or indeed, in drug delivery vehicles that may be designed specifically for at least one given modified particle. As alluded to herein, there may be more than one particle of interest comprised in the initial solution prepared for conventional spray drying (or the initial solution or solid material of any of the other process techniques referred to herein), such as a mixture of two or more particles of interest. In such a context, two or more active ingredients of interest or a combination of at least one pro-drug and at least one drug, or two or more drugs, or two or more agro-chemicals, may be present in the initial solution as solutes or as the initial solid material, depending on the desired end use post ultrasonic and optional microwave treatment. Suitable particles that are able to crystallise under the process conditions of the invention include active ingredients or drugs which can be formed into crystalline particles by the process of the present invention such as corticosteroids, β2-agonists, anticholinergics, leukotriene antagonists, inhalable proteins or peptides, mometasone furoate; beclomethasone dipropionate; budesonide; fluticasone; dexamethasone; flunisolide; triamcinolone; salbutamol; albuterol; terbutaline; salmeterol; bitolterol; ipratropium bromide; oxitropium bromide; sodium cromoglycate; nedocromil sodium; zafirlukast; pranlukast; formoterol; eformoterol; bambuterol; fenoterol; clenbuterol; procaterol; broxaterol; (22R)-6a,9a-difluoro-11b,21-dihydroxy-16a,17a-propylmethylenedioxy-4-pregnen-3,20-dione; TA-2005; tipredane; insulin; interferons; calcitonins; parathyroid hormones; and granulocyte colony-stimulating factor.

When more than one solid material is used, co-crystals may be formed. Co-crystals can be defined as crystalline complexes of two or more non-identical neutral molecular constituents, such as an active principal or desired precursor thereof, and a guest bound together in the crystal lattice through noncovalent interactions, preferably primarily hydrogen bonding. A guest may be another active principal or desired precursor thereof, or a co-crystal former.

The formation of pharmaceutical co-crystals involves incorporation of a given active pharmaceutical with another pharmaceutically acceptable molecule in the crystal lattice. The resulting multi-component crystalline phase will maintain the intrinsic activity of the parent active pharmaceutical while possessing a distinct physiochemical profile.

As used herein, the term "co-crystal former" denotes one or more additional molecules present in the same crystal structure as the active principal, or desired precursor thereof, which one or more additional molecules are capable of forming a supramolecular synthon with the active principal, or desired precursor thereof, by way of the intermolecular interactions characteristic of the bonding in a co-crystal.

in one embodiment, the co-crystal former comprises one or more molecules having at least one synthon forming moiety selected from the following group: ether, thioether, alcohol, carbonyl, thiol, aldehyde, ketone, thioketone, nitrate ester, phosphate ester, thiophosphate ester, ester, thioester, sulphate ester, carboxylic acid, phosphonic acid, phosphinic acid, sulphonic acid, sulphonamide, amide, primary amine, secondary amine, ammonia, tertiary amine, imine, thiocyanate, cyanamide, oxime, nitrile, diazo, organohalide, nitro, S-containing heterocyclic ring (such as thiophene), N-containing heterocyclic ring (such as pyrrole, imidazole or pyridine), O-containing heterocyclic ring (such as furan, epoxide or peroxide) and hydroxamic acid moieties.

In further embodiments, the guest may be present, for example, in order to form the co-crystal with the active principal or desired precursor thereof. It is contemplated that one or more guests may be included in a co-crystal. Accordingly, the guest is not required to have an activity of its own, although it may have some activity that does not overly derogate from the desired activity of the active agent. A non-active guest may be a compound where no beneficial pharmacological activity has been demonstrated and which are appreciably biologically non-toxic or pharmacologically benign. In some situations, the guest may have the same activity as or an activity complementary to that of the active agent. The guest may be another active principal or desired precursor thereof. For example, some guests may facilitate the therapeutic effect of an active principal or desired precursor thereof. For pharmaceutical formulations, the guest may be any pharmaceutically acceptable molecule(s) that form a co-crystal with the active principal or desired precursor or its salt.

The guest, or co-crystal former, may be an acid and behave in both a neutral manner but with noncovalent interactions (primarily hydrogen bonding), such as in the case of oxalic acid or other suitable carboxylic acids when prepared as a co-crystal with caffeine, and as a proton-donor when in the case of forming ionic salts such as in the reaction or proton-exchange with an amine for example. Similarly benzoic acid and succinic acid behave in a neutral manner (without formal proton exchange) when forming a co-crystal with fluoxetine hydrochloride or in a proton-exchange manner to form ionic salts such as sodium benzoate or sodium succinate. These compounds may be ionic guests in their own right. Neutral guests are preferably nonionic guests. Ionic guests are compounds or complexes having ionic bonding. The guest may be an acid that forms hydrogen bonds with the chloride (or other anion). Ionic guests are compounds or complexes having ionic character, as exemplified by ionic interaction and attraction. The guest may be an acid that forms hydrogen bonds with the pharmaceutical ingredient. For example, suitable guests which are acids include (but are not limited to): ascorbic acid, glucoheptonic acid, sebacic acid, alginic acid, cyclamic acid, ethane-1,2-disulfonic acid, 2-hydroxyethanesulfonic acid, 2-oxo-5 glutaric acid, naphthalene-1,5-disulfonic acid, nicotinic acid, pyroglutamic acid and 4-acetamidobenzoic acid. The solutes and active principles listed in the specification include the salt and/or solvates thereof. Co-crystals are described in WO2005/089375.

An example of a co-crystal of the present invention is sildenafil, or a pharmaceutically acceptable salt thereof, and acetylsalicylic acid (aspirin).

Other particles which may be made according to the invention include any drug or active ingredient that can be usefully delivered by inhalation, such as, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamime, pirbuterol, reproterol, rimiterol, salbutamol, salmeterol, terbutalin; isoetharine, tulobuterol, orciprenaline or (−)-4-amino-3,5-dichloro-a[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be appreciated by the person skilled in the art that where appropriate medicaments comprising active ingredients or drugs may be used in the form of salts (e.g. as alkali metal or amine salts or as acid addition salts) or as esters (e.g. lower alkyl esters) or as solvates (e.g. hydrates) to optimise the activity and/or stability of the medicament.

Particularly suitable medicaments for preparation with particles obtained in accordance with the process of the invention include anti-allergics, bronchodilators and anti-inflammatory steroids of use in the treatment of respiratory disorders such as asthma by inhalation therapy, for example fluticasone (e.g. as the propionate salt), cromoglycate (e.g. as the sodium salt), salbutamol (e as the free base or as the sulphate salt), salmeterol (e.g. as the xinafoate salt), terbutaline (e.g. as the sulphate salt), reproterol (e.g. as the hydrochloride salt), beclomethasone dipropionate (e.g. as the monohydrate), fluticasone propionate, (−)-4-amino-3,5-dichloro-α-[[[6-[2-(2-pyridinyl)ethoxy]hexyl]amino]-methyl]benzenemethanol glycopyrronium bromide, darotropium, aclidinium, tiotropium (eg. as bromide salt), theophyline, arofylline, zarfirlukast, monterlukast, carmoterol (eg. as the hydrochloride salt), formoterol (eg. as the fumarate salt), or indacaterol and physiologically acceptable salts and solvates thereof.

It will again be appreciated by the man skilled in the art that particles made by the process of the invention may contain a combination of two or more active ingredients as alluded to herein. Active ingredients may be selected from suitable combinations of the active ingredients mentioned hereinbefore. Thus, suitable combinations of bronchodilatory agents include ephedrine and theophylline, fenoterol and ipratropium, and isoetharine and phenylephrine.

Further suitable combinations of particles of active ingredients made according to the process of the invention include combinations of corticosteroids, such as budesonide, beclomethasone dipropionate and fluticasone propionate, with β2-agonists, such as salbutamol, terbutaline, salmeterol and formoterol and physiologically acceptable derivatives thereof, especially salts including sulphates.

The solid material is preferably a pharmaceutically active ingredient suitable for use in an inhalation formulation, preferably fluticasone propionate, budesonide, salbutamol, formoterol or mixtures of two or more thereof.

Further suitable combinations of particles of active ingredients made according to the process of the invention include combinations such as Formoterol and Fluticasone; Beclomethasone and Formoterol; Formoterol and Mometasone; Indacaterol and Mometasone; Ipatropium bromide and Albuterol; Salbutamol and Albuterol; Tiotropium bromide and Formoterol; Glycopyrronium bromide and Indacaterol; Formoterol and Ciclesonide; Beclomethasone/Salmeterol.

In another embodiment three ingredients can be combined including combinations of corticosteroid, bronchodilator (such as a beta agonist), and anticholinergic agent. One example is fluticasone/salmeterol/tiotropium bromide.

Other examples of particles obtainable by the process of the invention may include a cromone which may be sodium cromoglycate or nedocromil, or a carbohydrate, for example, heparin.

The particles made by the process of the invention may comprise an active ingredient suitable for inhalation and may be a pharmacologically active agent for systemic use. For example, such active particles may comprise peptides or polypeptides or proteins such as Deoxyribonuclease (DNase), leukotines or insulin (including pro-insulins), cyclosporin, interleukins, cytokines, anticytokines and cytokine receptors, vaccines, growth hormone, leuprolide and related analogues, intereferons, desmopressin, immunoglobulins, erythropoeitin and calcitonin.

Alternatively, the active ingredient made by the process of the invention may be suitable for oral administration. A drug for oral administration may be one of the systemic drugs mentioned above. The active ingredient may be a substance which exhibits low solubility in the digestive tract, for example, magnesium trisilicate, calcium carbonate and bismuth subnitrate. Organic compounds may include, for example, all products of combinatorial chemistry, rosiglitazone and other related glitazone drugs, hydrochlorothiazide, griseofulvin, lamivudine and other nuclease reverse transcriptase inhibitors, simvastatin and other statin drugs, benzafibrate and other fibrate drugs and loratidine, and any other physiologically tolerable salts and derivatives thereof.

Pharmaceutical excipients suitable for processing according to the present invention include, for example, carbohydrates especially monosaccharides such as fructose, glucose and galactose; non-reducing disaccharides such as sucrose, lactose and trehalose; non-reducing oligosaccharides such as raffinose and melezitose; non reducing starch derived polysaccharides products such as maltodextrins, dextrans and cyclodextrins; and non-reducing alditols such as mannitol and xylitol. Further suitable excipients include cellulose preparations such as, for example, maize starch, wheat starch, rice starch, potato starch, gelatin, gum tragacanth, methyl cellulose, hydroxypropylmethylceliulose, sodium carboxymethylcellulose, and/or polyvinylpyrrolidone (PVP). Mixtures of two or more of any of the above excipients are also envisaged.

For use in medicine, the salts of the compounds of this invention refer to non toxic "pharmaceutically acceptable salts." FDA approved pharmaceutical acceptable salt forms (International J. Pharm. 1986, 33,201 217; J. Pharm. Sci., 1977, January 66 (1), p 1) include pharmaceutically acceptable acidic/anionic or basic/cationic salts.

Pharmaceutically acceptable salts of the acidic or basic compounds of the invention can of course be made by conventional procedures, such as by reacting the free base or acid with at least a stoichiometric amount of the desired salt forming acid or base.

Pharmaceutically acceptable salts of the acidic compounds of the invention include salts with inorganic cations such as sodium, potassium, calcium, magnesium, zinc, and ammonium, and salts with organic bases. Suitable organic bases include N methyl D glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

Where the particles of active ingredient(s) prepared by the process of the present invention are agrochemically active, the active ingredient may for example be a plant growth regulator, herbicide, and/or pesticide, for example insecticide, fungicide, acaricide, nematocide, miticide, rodenticide, bactericide, molluscicide or bird repellant.

Examples of organic water-insoluble agrochemical active ingredients made according to the process of the invention include insecticides, for example selected from the group consisting of carbamates, such as methomyl, carbaryl, carbofuran, or aldicarb; organo thiophosphates such as EPN, isofenphos, isoxathion, chlorpyrifos, or chlormephos; organo phosphates such as terbufos, monocrotophos, or terachlorvinphos; perchlorinated organics such as methoxychlor; synthetic pyrethroids such as fenvalerate; nematicide carbamates, such as oxamyl herbicides, for example selected from the group consisting of triazines such as metribuzin, hexaxinone, or atrazine; sulfonylureas such as 2-chloro-N-[(4-methoxy-6-methyl-1,3,5-triazin-2-yl) aminocarbonyl]-benzenesulfonamide; uracils (pyrimidines) such as lenacil, bromacil, or terbacil; ureas such as linuron, diuron, siduron, or neburon; acetanilides such as alachlor, or metolachlor; thiocarbamates such as benthiocarb (SATURN), triallate; oxadiazol-ones such as oxadiazon; phenoxyacetic acids such as 2,4-D; diphenyl ethers such as fluazifop-butyl, acifluorfen, bifenox, or oxyfluorfen; dinitro anilines such as trifluralin; glycine phosphonates such as glyphosate salts and esters; dihalobenzonitriles such as bromoxynil, or ioxynil; fungicides, for example selected from the group consisting of nitrilo oximes such as cymoxanil (curzate); imidazoles such as benomyl, carbendazim, or thiophanate-methyl; triazoles such as triadimefon; sulfenamides such as captan; dithiocarbamates such as maneb, mancozeb, or thiram; chloronated aromatics such as chloroneb; dichloro anilines such as iprodione; aphicides, for example selected in the group consisting of carbamates, such as pirimicarb; miticides, for example selected from the group consisting of propynyl sulfites such as propargite; triazapentadienes such as amitraz; chlorinated aromatics such as chlorobenzilate, or tetradifan; and dinitrophenols such as binapacryl.

The organic water-insoluble agrochemical active ingredients may be comprised in the particles produced according to the present invention as a mixture of several ingredients. Especially preferred organic water-insoluble agrochemical active ingredients are atrazine, cymoxanil, chlorothalanil, cyproconazole, and tebuconazole.

It will be appreciated that the solvent should be selected as being suitable for a particular active ingredient or active precursor thereof. Corticosteroids, such as budesonide, beclomethasone dipropionate and fluticasone propionate may be dissolved in dichlormethane or methanol. β2-agonists, such as salmeterol xinafoate and formoterol fumarate, may be dissolved in methanol.

Following a conventional separation step, such as cyclonic separation, the dried particle is placed in or on an ultrasonic chamber, sieve or a conveyor and then subjected to ultrasonic irradiation to form crystals, or to anneal and/or stabilise amorphous structures of a desired MMAD as hereinbefore described. The particles are subject to the operating vicinity of the ultrasonic probe if used, or of an ultrasonic energy transducer. The ultrasonic energy may be applied continuously or in a discontinuous manner, such as by pulsed application. Any suitable source of ultrasonic irradiation may be used providing there is a means for the particles to come into contact with the resonating surface. An ultrasonic probe may, for example, be inserted into a dry powder mixing vessel, an ultrasonic emitter may be contained in the mixing vessel, or the mixing vessel may be housed in an ultrasonic bath or it may have an ultrasound transducer fixed to the external walls of the dry powder mixing vessel. In the simplest form loosely packed materials in a dry powder mixing or blending chamber will come into contact with a ultrasound vibrating surface whilst being mechanically agitated or fluidized with gas. The ultrasound may be provided by means of an ultrasound actuated sieve, an ultrasonic vibrating conveyor belt, or ultrasonic resonating chamber. Ultrasonic actuated sieves are known in the fine chemicals and pharmaceutical processing industries.

The amplitude and frequency of the ultrasound waves affects the rate of nucleation and crystal growth. The frequency of the ultrasound waves may for example be from 16 kHz to 1 MHz, preferably from 10-500 kHz, more preferably from 10-100 kHz such as at 10, at 20, 40, 60, 80, or 100 kHz or at any frequency therebetween, such as, 30 kHz or 50 kHz.

The ultrasonic irradiation is employed at an amplitude or power density that is appropriate for the production of crystals of the desired size, for a pre-determined application. For laboratory probe systems with an emitting face of, for example 80 $cm^2$, the amplitude selected may be from about 1-30 μm, typically from 3-20 μm, preferably from 5-10 μm, for example, 6 μm. Probes having a probe face surface area of 8 $cm^2$ and a power requirement of from 5-80 W, provide a power density of from about 0.6-12.5 $W/cm^2$ using an amplitude of 2-15 μm. In larger systems, preferably such as those embodied in WO 03/101577, comprising transducers bonded onto the flow cell, for example a 6 liter flow cell, the power density for the transducers employed may be from 10-100 W/L, preferably from 30-80 W/L, and more preferably from 50-75 W/L, for example 60 W/L or 70 W/L. The present invention is particularly suitable for industrial scale production.

The residence time of the mixed components in the ultrasonic flow cell may be preferably greater than 0.1 ms, more preferably greater than 1 ms, more preferably greater than 1 minute, for example between 1 second and 24 hours, more preferably between 1 minute and 6 hours, more preferably between 5 minutes and 1 hour.

Generated crystals may be collected as a dry powder by conventional means.

The particles produced according to the invention are substantially crystalline and show a reduced tendency of moisture adsorption which contributes to increase their physical and chemical stability. "Substantially crystalline" means the degree of crystallinity of the particles, expressed as weight % of the crystalline particle with respect to the total weight of the particle, is greater than 90%, preferably greater than 93%, even more preferably greater than 95%. Said particles also exhibit excellent dispersion properties allowing to easily obtaining homogenous formulations, in particular when the particles are formulated as dry powders for inhalation. The degree of crystallinity of the particle may be determined using Differential Scanning Calorimetry (DSC), X-ray powder diffraction or other techniques known to the skilled person such as microcalorimetry, preferably DSC.

In one embodiment the solid material is a corticosteroid and preferably is any corticosteroid insoluble or poorly-soluble in water according to the definition of solubility given in the European Pharmacopoeia Ed. $4^{th}$, 2002, which can be utilised by inhalation for the prevention and/or treatment of respiratory diseases. Preferably the corticosteriod has a single therapeutical dose higher than 50 μg, preferably equal to or higher than 80 μg, more preferably equal to higher than 100 μg.

Preferably, the corticosteroid is selected from the group consisting of beclomethasone dipropionate (BDP), budesonide, ciclesonide, mometasone and esters thereof, such as furoate, and fluticasone and esters thereof, such as propionate and furoate. In a preferred embodiment of the invention the corticosteroid is budesonide or fluticasone and salts or esters thereof.

Preferably the active particles of the invention have a volume diameter of less than 10 μm, more preferably at least 90 wt % of the active ingredient particles in a given composition have a diameter equal to or lower than 10 μm as determined by measuring the characteristic equivalent sphere diameter, known as volume diameter, by laser diffraction as described above, preferably using a Malvern or equivalent apparatus. The parameters taken into consideration are the volume diameters (VD) in microns of 10%, 50% and 90% of the particles expressed as d(10), d(50) and d(90), respectively, which correspond to the mass diameter assuming a size independent density for the particles.

Preferably no more than 10 wt % of said particles have a volume diameter d(10) lower than 0.8 μm, preferably no more than 50 wt % of said particles have a volume diameter d(50) lower than 2.0 μm, preferably at least 90 wt % of said particles have a volume diameter d(90) equal to or lower than 10 μm. Preferably 100 wt % of said particles have a volume diameter equal to or lower than 10 μm.

The active ingredients in the particles of the invention are substantially in a pure form. "Substantially in a pure form" means at least 95% w/w pure, preferably at least 98% or at least 99% w/w. The chemical purity may be determined according to methods known to the skilled person such as high-performance liquid chromatography (HPLC).

In another aspect the present invention provides a formulation for administration by inhalation comprising the particles of the invention. The particles may be formulated into said formulation together with one or more pharmaceutically acceptable excipients, additives, diluents or carriers. For example, the formulation is provided in the form of suspension in a propellant as aerosol carrier to be administered by pressurized metered dose inhalers (pMDI).

The suspension formulation may comprise additional excipients such as surfactant, and wetting agent.

In a preferred embodiment, the formulation is provided in the form of dry inhalation powder, more preferably in the form of interactive ordered mixtures, i.e. by diluting the particles of the invention in a pharmacologically inert physiologically acceptable excipient consisting of coarser particles.

Advantageously, said powder formulation for inhalation may comprise the particles according to the invention and coarse particles of a physiologically acceptable excipient, hereinafter "carrier particles", e.g. particles having a mass median particle diameter (MMD) higher than 50 μm and preferably the MMD comprised between 50 μm and 500 μm, more preferably between 150 and 400 μm, even more preferably between 210 and 355 μm. In another embodiment, the coarse particles have a MMD comprised between 90 and 150 μm. The MMD is the particle diameter that divides the frequency distribution in half; fifty percent of the aerosol mass has particles with a larger diameter, and fifty percent of the aerosol mass has particles with a smaller diameter.

Preferably at least 50% by weight of the carrier particles have a diameter of less than 500 μm, more preferably at least 80% by weight of the carrier particles have a diameter of less than 500 μm, more preferably at least 90% by weight of the carrier particles have a diameter of less than 500 μm, more preferably 100% by weight of the carrier particles have a diameter of less than 500 μm.

The physiologically acceptable excipient may be constituted of any amorphous or crystalline physiologically acceptable pharmacologically-inert material of animal or vegetable source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol may also be used. The most preferred material is α-lactose monohydrate.

Examples of commercial lactose are Capsulac™ and Pharmatose™. An example of commercial mannitol is Pearlitol™.

The formulation may be provided in the form of a suspension or a powder to be administered by breath activated nasal inhalers.

Said powder formulation may be administered by inhalation with any type of DPIs known in the art.

DPIs can be divided into two basic types: i) single dose inhalers, for the administration of pre-subdivided single doses of the active compound; ii) multidose dry powder inhalers (MDPIs), either with pre-subdivided single doses or pre-loaded with quantities of active ingredient sufficient for multiple doses. On the basis of the required inspiratory flow rates (l/min) which in turn are strictly depending on their design and mechanical features, DPIs are divided in: i) low-resistance devices (>90 l/min); ii) medium-resistance devices (about 60 l/min); iii) high-resistance devices (about 30 l/min).

Having regard to the pharmacological activity of the active ingredients, the particles of the invention may be indicated for the prevention and/or treatment of mild, moderate or severe acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis may also benefit by their use.

For administration via inhalation, the particulate active ingredients produced according to the present process are preferably formulated with carrier particles. Said active ingredient may be present in 0.1%-90% by weight of the formulation, preferably 0.25%-50%, more preferably 1-25% by weight of the formulation. Preferably, the carrier particles may be present in an amount of 10-99.9% by weight of the formulation, more preferably 50%-99.75%, more preferably 75-99% by weight of the formulation.

In a particularly preferred embodiment, the active ingredient in the particle produced according to the present invention comprises (preferably consists essentially of) fluticasone propionate, budesonide, formoterol, salmeterol, beclomethasone or betamethosone, and mixtures and co-crystals thereof. This list also encompasses salts, hydrates and solvates of said compounds.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention may be measured by conventional techniques, for example by using a Next Generation Impactor (NGI) with pre-separator for example by cascade impaction or by the "Twin lmpinger" analytical process. As used herein reference to the "Twin lmpinger" assay means "Determination of the deposition of the emitted dose in pressurised inhalations using apparatus A" as defined in British Pharmacopoeia 1988, pages A204-207, Appendix XVII C. Such methods involve filling the pre-separator with HPLC mobile phase and the cups of the NGI cups were coated with 1% v/v silicone oil in hexane to eliminate particle bounce. Typically four individual capsules of the same formulation are discharged into the NGI under prescribed conditions. Following aerosolization, the NGI apparatus is dismantled and the inhaler, capsules and each part of the NGI washed down into known volumes of HPLC mobile phase. The mass of drug deposited on each part of the NGI can then be determined by HPLC. The FPD determined represents the mass of drug collected on stages 3-8 of the NGI. The FPF emitted dose is also determined. The aerosolisation efficiency as determined by percentage fine particle fraction (% FPF) or respirable fraction is also assessed.

Such techniques enable the "respirable fraction" of the aerosol formulations to be calculated. As used herein reference to "respirable fraction" means the amount of active ingredient collected in the lower chamber in the NGI per actuation expressed as a percentage of the total amount of active ingredient delivered per actuation using the method described above.

The propellants for use in the inhalable formulations including particles according to the present invention comprise any fluorocarbon or hydrogen-containing chlorofluorocarbon or mixtures thereof having a sufficient vapour pressure to render them effective as propellants. Preferably the propellant will be a non-solvent for the medicament. Suitable propellants include conventional hydrogen-containing chlorofluorocarbons, non-chlorofluorocarbons, hydrogen-containing fluorocarbons and perfluorocarbons, and the like. In particular the propellants HFA 134a, and HFA 227 or mixtures thereof may be advantageously used.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene.

Suitable valves are commercially available from manufacturers well known in the aerosol industry, for example, from Valois, France (e.g. DF10, DF30, DF60), Bespak plc, UK (e.g. BK300, BK356) and 3M-Neotechnic Ltd, UK (e.g. SpraymiserW).

Conventional bulk manufacturing methods and machinery well known to those skilled in the art of pharmaceutical aerosol manufacture may be employed for the preparation of large scale batches for the commercial production of filled canisters.

Typically, in batches prepared for pharmaceutical use, each filled canister is check weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff. Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Suitable daily doses, may be, for example in the range 50 to 200 µg of salmeterol, 100 to 1000 µg of salbutamol, 50 to 2000 µg of fluticasone propionate or 100 to 2000 µg of beclomethasone dipropionate, depending on the severity of the disease.

Thus, for example, each valve actuation may deliver 25 µg salmeterol, 100 µg salbutamol, 25, 50, 125 or 250 µg fluticasone propionate or 50, 100, 200 or 250 µg beclomethasone dipropionate. Typically each filled canister for use in a metered dose inhaler contains 100, 160 or 240 metered doses or puffs of medicament.

The filled canisters and metered dose inhalers described herein comprise further aspects of the present invention.

The invention will now be described with reference to the accompanying examples and figures. It is to be understood that the examples and figures are not to be construed as limiting the scope of the invention in any manner.

BRIEF DESCRIPTION OF THE DRAWINGS

The process of the invention may be carried out using conventional equipment as shown in the accompanying figures in which.

DETAILED DESCRIPTION OF THE INVENTION

Figure 6:
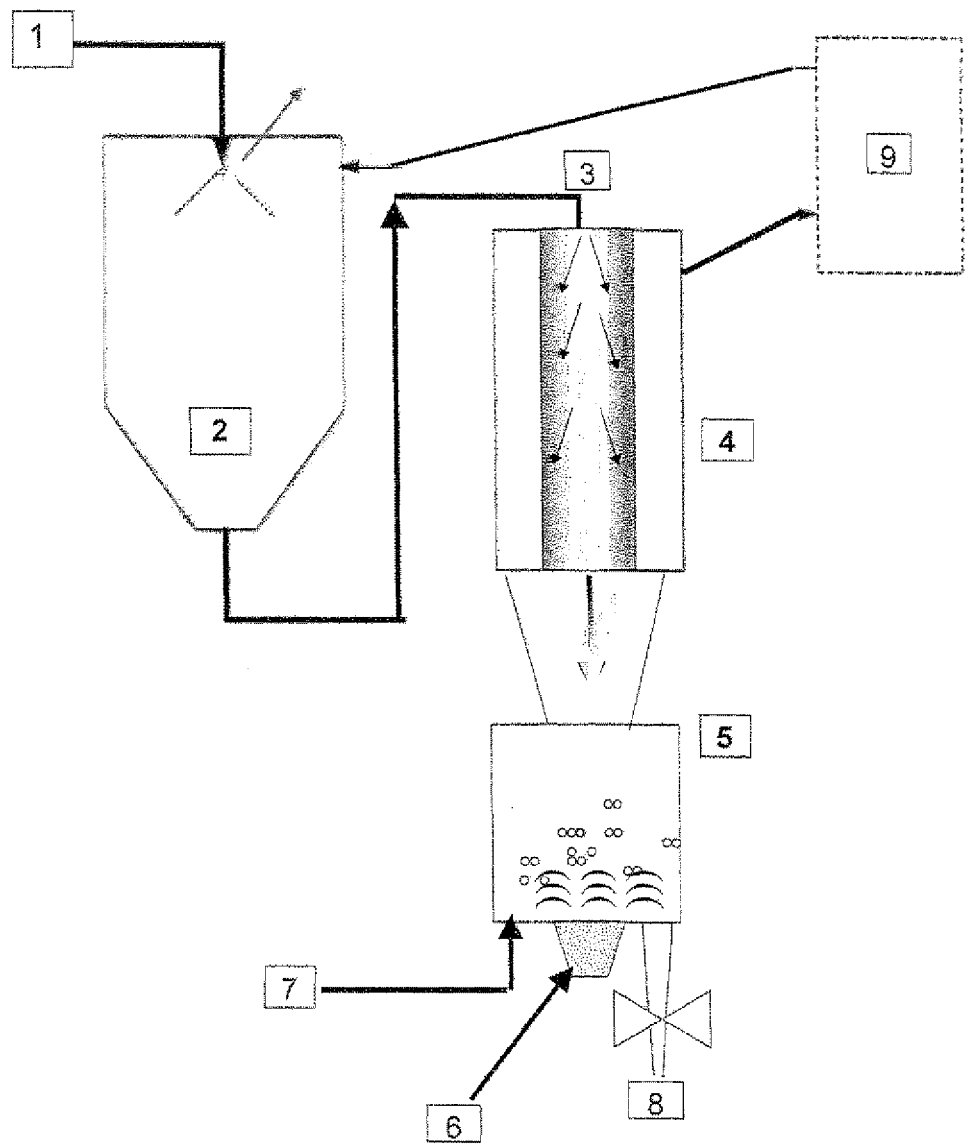
FIG. 6, shows a diagrammatic representation of a conventional spray drying equipment whereby the dry solid collection chamber is replaced by an ultrasonic cell having a single bonded ultrasonic transducer to create a resonating surface on the base.

FIG. 6 shows a spray drying with ultrasound apparatus comprises a liquid feed chamber 1, spray drying atomiser with heated gas inlet, evaporation chamber 2, particle inlet 3, bag filter particle separator 4, continuous ultrasonic treatment chamber 5, with bonded ultrasonic transducer 6. The conventionally treated spray dried powder is deposited directly into an ultrasonic flow cell chamber 5. Concurrently, the chamber is heated so as to behave as an oven or heated by way of warm gas input 7. Whilst not an essential design feature of this invention, concurrently, the chamber is heated so as to behave as an oven or heated by way of warm gas input 7. The thermal input will be substrate dependent but could be typically from 25° C. to 80° C. Upon complete crystalline conversion heat may be applied to remove any residual solvent. Alternatively the crystalline powder may be formally dried by conventional techniques. Heat can therefore be applied during the application of ultrasound, and/or after the application of ultrasound. Ultrasonic transducer 6 irradiates the powder with ultrasonic energy. Upon complete conversion to a crystalline solid the particles are discharged 8. Clean gases are recycled through unit 9. The ultrasonic radiation is continued as long as necessary until the desired particle size and crystallinity is achieved. Naturally the feed stream to the spray dryer is balanced with the rate at which powder is removed. The flow rates are controlled such that the residence time in the ultrasonic flow cell chamber 5, is for example, 10 s to 1 hr. By adjusting the power of the ultrasound, and the residence time in chamber 5, the particle size and morphology can be controlled. The ultrasound has the additional benefit that any crystal or indeed amorphous particle deposits within the chamber 5, tend to be removed from the resonating surfaces. Obviously the amorphous particles will remain in the resonating ultrasonic chamber as long as necessary to effect transformation to crystalline particles. The degree of crystallinity may be measured by DSC.

Figure 7:
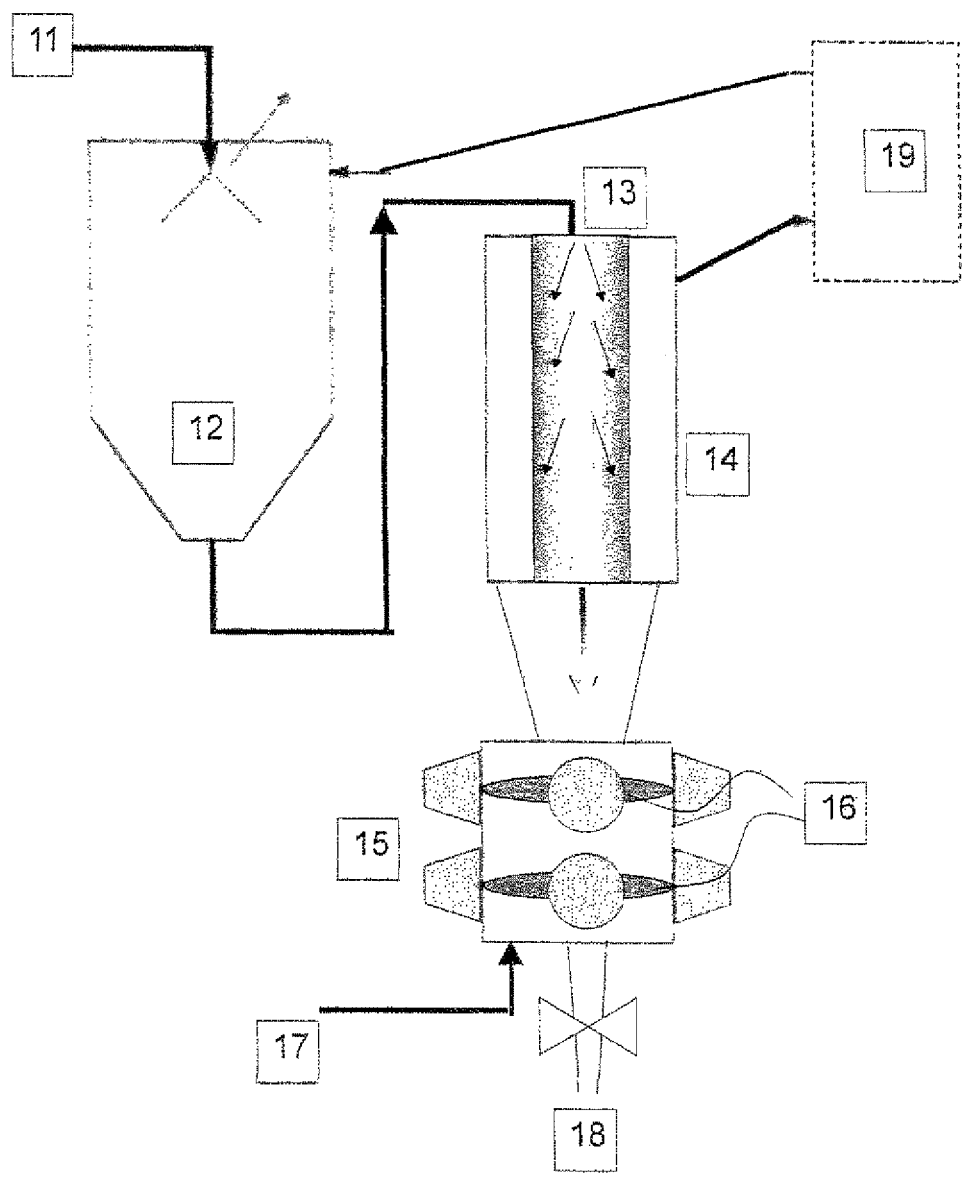
FIG. 7 shows a diagrammatic representation of a conventional spray drying equipment whereby the dry solid collection chamber is replaced by an ultrasonic vibrating sieving apparatus.

Referring to FIG. 7, the spray drying with ultrasound apparatus is of a similar configuration to that of FIG. 6 except that ultrasonic chamber 15 contains a plurality of ultrasonic activated sieve meshes 16 via transducers attached to the sieves 16. The vibrating sieves impart energy to the particles with sufficient intensity to cause dispersion, deagglomeration and amorphous to crystalline or metastable to stable-crystalline conversion, and by adjusting the power of the ultrasound, and the residence time in the chamber 15, the particle size and morphology can therefore be controlled. Concurrently, the chamber is heated so as to behave as an oven or heated by way of warm gas input 17. The residence time can be adjusted by using appropriately fine sieves so there is a useful hold-up in the chamber 15 prior to gravitational fall to the base of the chamber 15 and to discharge 18. The ultrasonic sieving has the additional benefit that particles may be fractionated by virtue of their varying size. The feed stream to the spray dryer is balanced with the rate at which powder is removed. The flow rates are controlled such that the residence time in the ultrasonic flow cell chamber 15, is for example, 10 s to 1 hr. Clean gases are recycled through unit 19.

Figure 8:
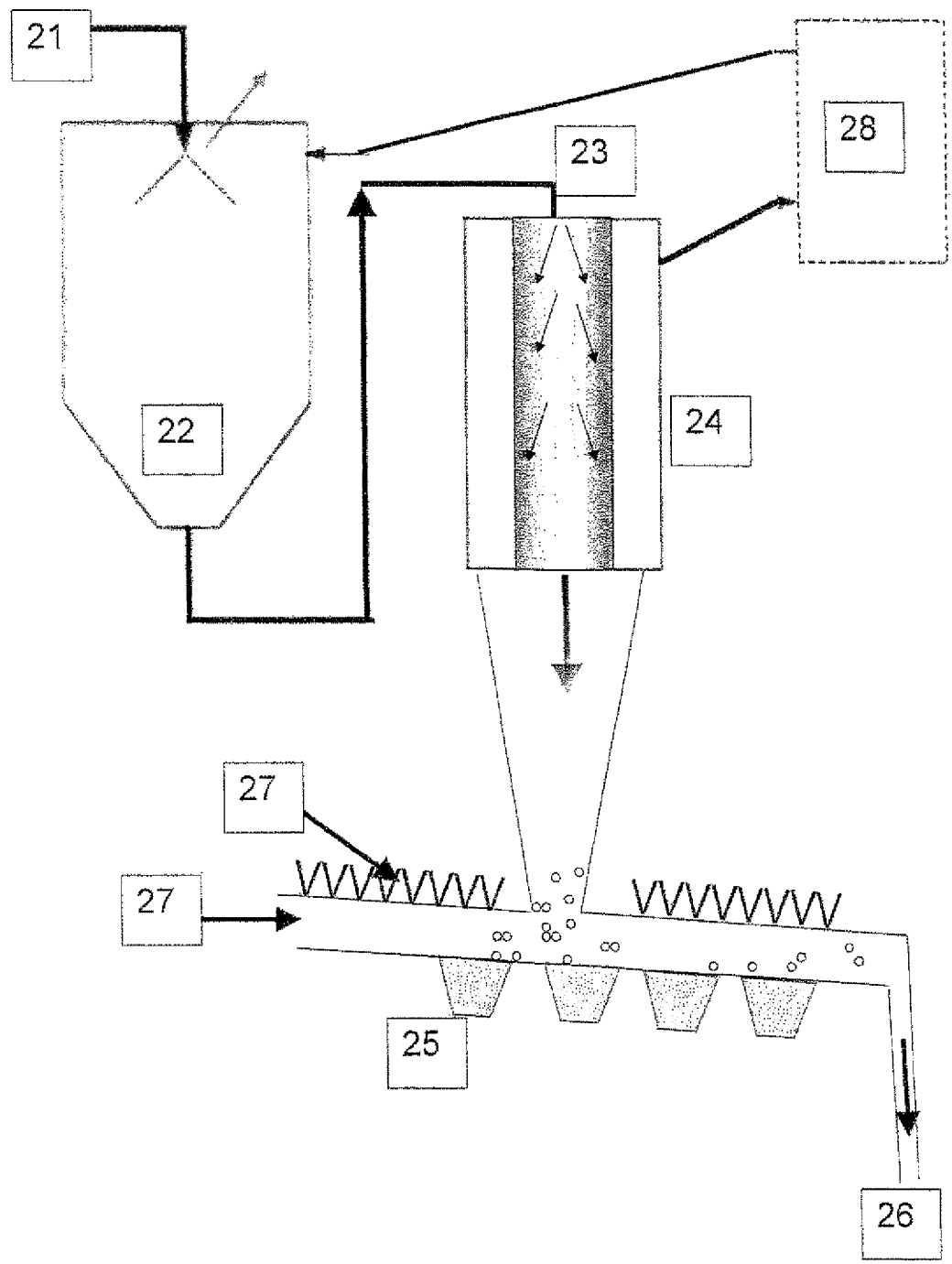
FIG. 8 shows a diagrammatic representation of a conventional spray drying equipment whereby the dry solid collection chamber is replaced by ultrasonic resonating surface chamber with gradient for gravity discharge.

Referring to FIG. 8, the spray drying with ultrasound apparatus is of a similar configuration to that of FIGS. 6 and 7 except that ultrasonic chamber 25 is a continuous particle collection device whereby the particles fall on to a resonating surface which has ultrasonic transducers located on the external underside surface. The resonating surface imparts energy to the particles with sufficient intensity to cause dispersion, deagglomeration and amorphous to crystalline or metastable to stable-crystalline conversion. The ultrasound has the additional benefit that any crystal deposits within the chamber 25 tend to be removed from the surfaces. Concurrently, the chamber 25 is heated with heating source 27 so as to behave as an oven or heated by way of warm gas input 27. The particles are treated continuously in chamber 25, and fed through the system by either gravitational fall to discharge 26 or by flow or warm gas 27. Clean gases are recycled through unit 28.

Figure 9:
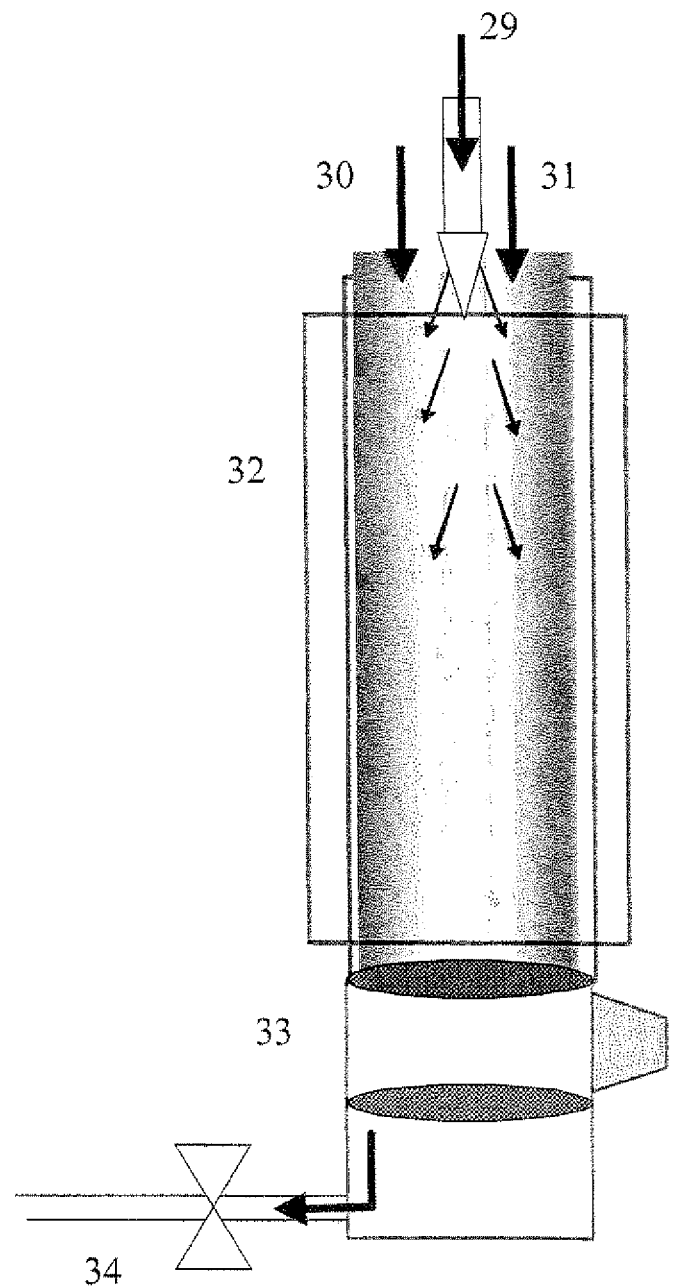
FIG. 9 shows a diagrammatic representation of a conventional spray drying equipment whereby the dry solid collection chamber is replaced by a continuous particle collection and ultrasonic sieving device.

Referring to FIG. 9, the spray drying with ultrasound apparatus is of a similar configuration to that of FIGS. 6 and 7 except that ultrasonic chamber 33 is a continuous particle collection and sieving device whereby the particles fall on to a resonating sieve surface which is coupled to an ring sonotrode or has ultrasonic transducers located on the external underside surface. The system is designed to spray dry the solution, by atomizing the solution through atomizer 29 and with additional heating provided by warm gas inputs 30 and 31 and with the heating jacket 32, to generate particles that are immediately collected and sieved using ultrasound activated sieve 33. The resonating surface of 33 imparts energy to the particles with sufficient intensity to cause dispersion, deagglomeration and amorphous to crystalline or metastable to stable-crystalline conversion. The ultrasound has the additional benefit that any crystal deposits within the chamber 33 (causing sieve blinding) tend to be removed from the surfaces. Concurrently, the chamber 33 is heated with heating source so as to behave as an oven or heated by way of warm gas input 30 and 31. The particles are treated continuously in chamber 33.

The term "comprising" means "including" as well as "consisting" e.g. a composition "comprising" X may consist exclusively of X or may include something additional e.g. X+Y.

Unless defined otherwise, the word "substantially" does not exclude "completely" e.g. a composition which is "substantially free" from Y may be completely free from Y. Where necessary, the word "substantially" may be omitted from the definition of the invention.

"Optional" or "optionally" means that the subsequently described event of circumstances may or may not occur, and that the description includes instances where said event or circumstance occurs and instances in which it does not.

EXAMPLES

Example 1

Fenoterol Hydrobromide for Inhalation

Figure 4:
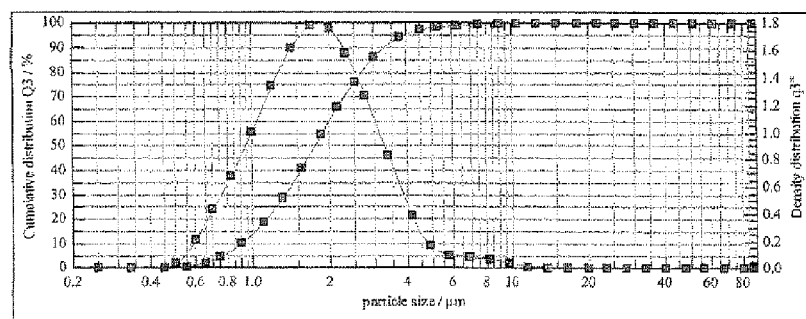
FIG. 4 shows a Sympatec particle size distribution of spray dried fenoterol hydrobromide with dry powder ultrasound treatment of the present invention.

Fenoterol hydrobromide (5 g) was dissolved in 100 mL of methanol. The samples of Fenoterol hydrobromide powder collected in the ultrasonic chamber were produced using a Büchi-290 laboratory-scale spray dryer (Büchi, Switzerland). The solution was atomized using nitrogen at 7 bar flowing at approximately at 10 Lpm (Liter/minute). The aspirator was set at 100% and flow rate of solution was set to 10 Lpm. The gas temperature was set to 120° C. Fenoterol hydrobromide particles were collected from both the cyclone separator and the PTFE bag filter assembly. The resultant amorphous particles contained 3000 ppm (0.3% w/w)

residual methanol. The particles were placed into an ultrasonic chamber fitted with a 20 kHz ultrasonic transducer on its base (Prosonix SL 10) as shown in FIG. 8. The chamber was heated to 40° C. using a thermoregulated water jacket. Ultrasound at 20 W power was applied between 30 minutes and 2 hour. The resulting particles were characterized by optical microscopy and DSC (Differential Scanning Calorimetry). The size of the particles were typically in the range of 1-7 μm. In this specific example d(10)=0.91 μm; d(50)=1.76 μm; d(90)=3.38 μm (see FIG. 4).

Figure 1:
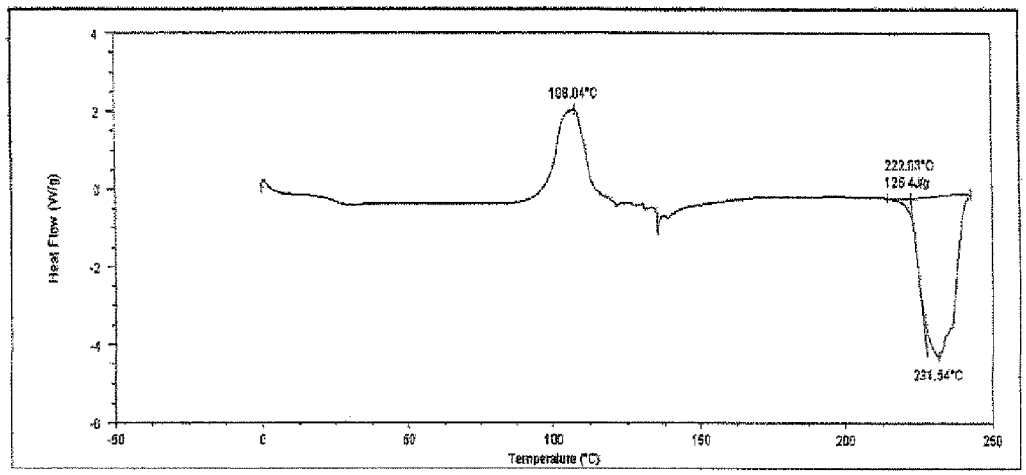
FIG. 1 shows a DSC of amorphous fenoterol hydrobromide
Figure 2:
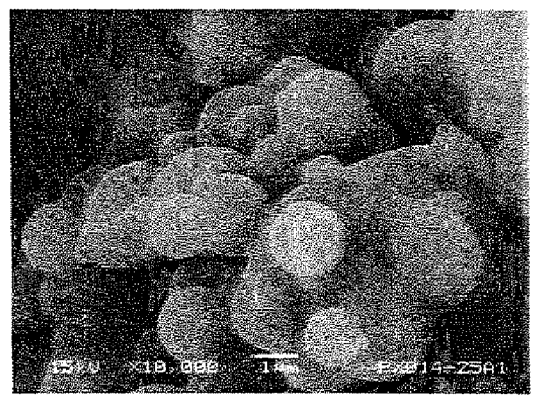
FIG. 2 shows an SEM image of amorphous fenoterol hydrobromide
Figure 3:
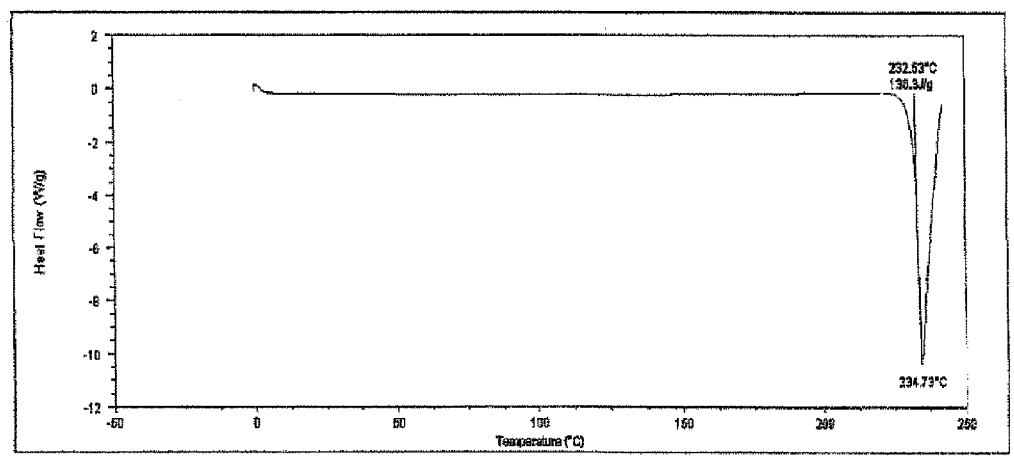
FIG. 3 shows DSC of crystalline fenoterol hydrobromide with dry powder ultrasound treatment of the present invention
Figure 5:
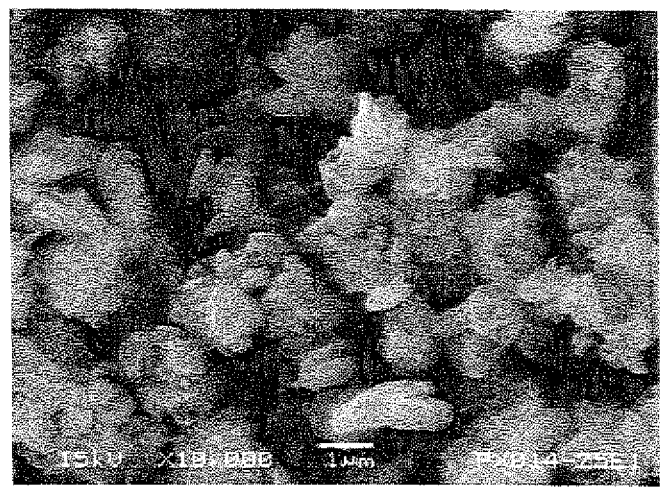
FIG. 5 shows single electron microscopy of spray dried fenoterol hydrobromide with dry powder ultrasound treatment of the present invention.

FIGS. 1 and 3 compare the DSC traces for the amorphous particles after initial spray drying but before ultrasonic treatment and particles after ultrasonic treatment, and demonstrate there is clear indication that application of ultrasound to spray dried particles modifies the physical characteristics of particles. For spray dried material not subject to ultrasonic treatment (FIG. 1) the exotherm (positive peak on trace) at 108° C. is indicative of amorphous to crystalline transformation in the DSC apparatus. For the particles prepared as described in this invention (FIG. 3) the endotherm (negative peak) at 234° C. (solid trace) and complete absence of a peak at 108° C. is indicative of a highly crystalline product. There is definite improvement in crystalline characteristic of processed material. In addition the SEM images FIGS. 2 and 5 show clear difference in morphology before and after ultrasonic treatment.

Example 2

Budesonide (4 g) was dissolved in acetone (100 mL) and the solution spray dried using a Büchi-290 laboratory-scale spray dryer (Buchi, Switzerland). The solution was atomized using nitrogen at 4-4.5 bar flowing at approximately at 10 Lpm (Liter/minute). The aspirator was set at 100% and flow rate of solution was set to 15-17 Lpm. The inlet gas temperature was set to 70-75° C. and the corresponding outlet temperature was 38-42° C. Budesonide particles were collected from both the cyclone separator and the PTFE bag filter assembly.

The spray dried budesonide was then transferred to ultrasonic sieve assembly. The system comprises of common laboratory ring sieves (according to DIN ISO 3310/1 or ASTM E 11-95) with diameters of 200 mm or 8 inch. A ring 24 kHz sonotrode that fits around the sieve is excited by the ultrasonic processor UIS250L (supplied by Hielscher). The ring sonotrode (RIS) transmits the oscillation via the sieve frame to the screening surface. With the help of the clamping fixtures the neighbouring sieves are also excited. Ultrasound at 250 W power was applied between 30 minutes and 2 hour (amplitude 100%, constant sonication, 100% pulse set-up). The resulting particles were characterized by optical microscopy, TGA (Thermo gravimetric analysis) and DSC (Differential scanning calorimetry).

Figure 10:
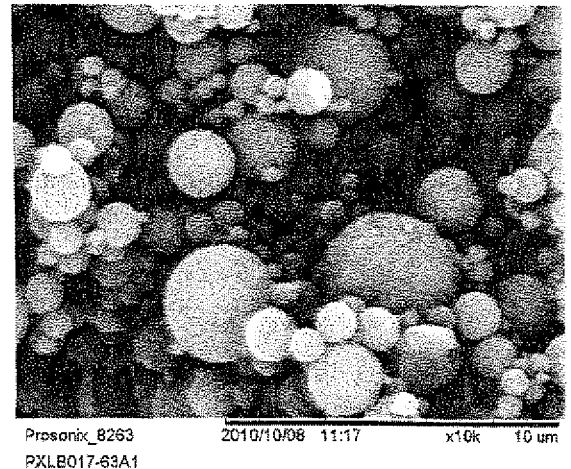
FIG. 10 shows single electron microscopy of spray dried budesonide particles which are not according to the invention.
Figure 11:
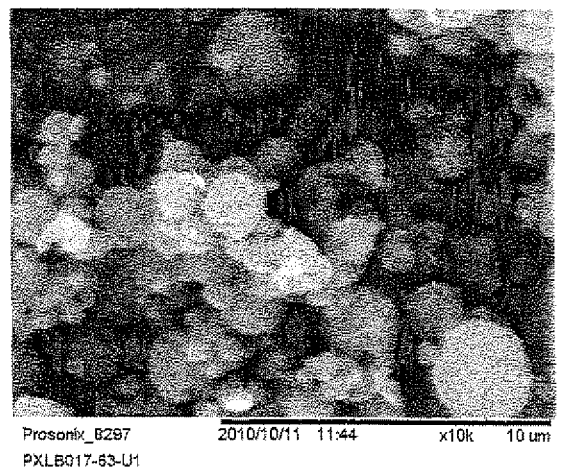
FIG. 11 shows single electron microscopy of ultrasonically treated spray dried budesonide particles according to the invention.
Figure 12:
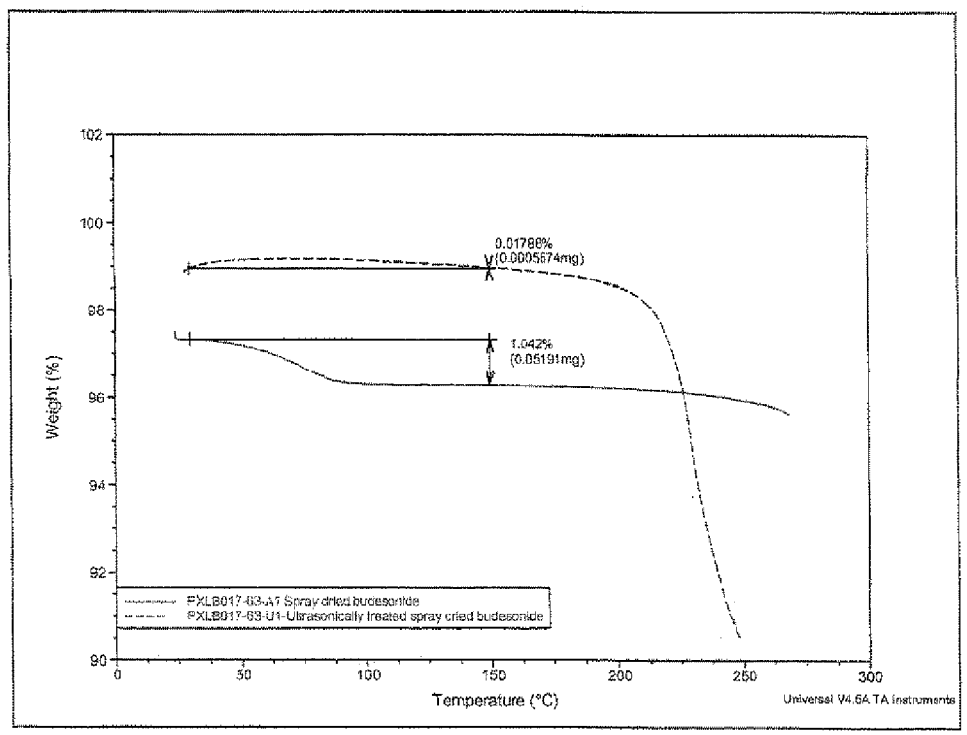
FIG. 12 shows a thermogravimetric analysis of budesonide particles.
Figure 13:
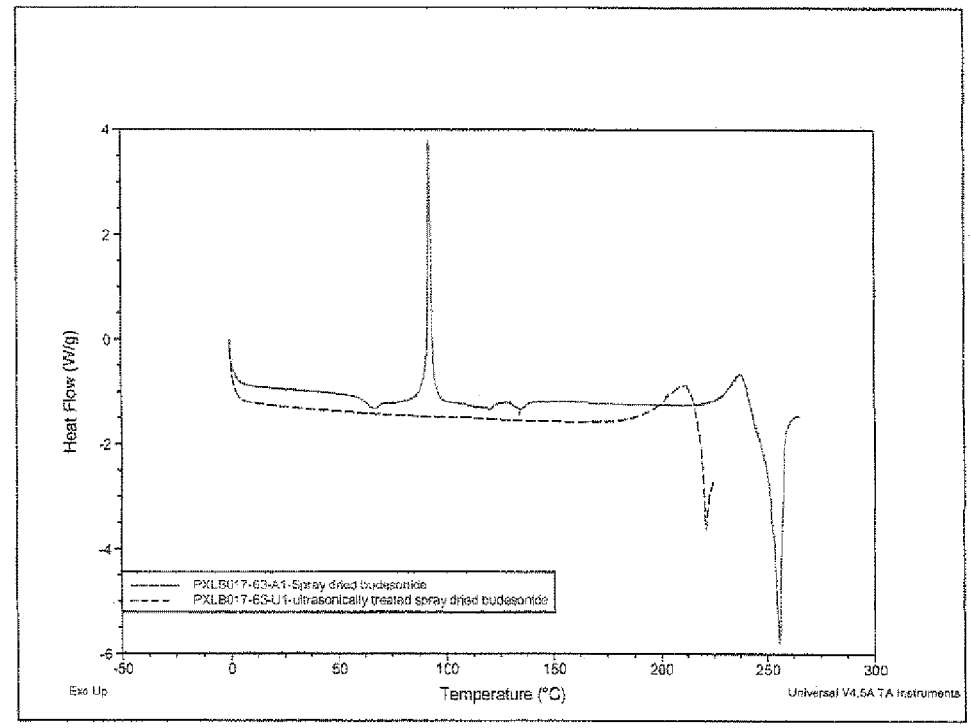
FIG. 13 shows a DSC thermogram of budesonide particles.

FIG. 10 shows an SEM image of spray dried budesonide particles before ultrasonic treatment. FIG. 11 shows an SEM image of the ultrasonically treated spray dried budesonide particles. FIGS. 12 and 13 show the thermal analysis for the amorphous particles obtained after initial spray drying but before ultrasonic treatment and particles after ultrasonic treatment. FIG. 12 shows the TGA data and FIG. 13 shows the DSC data. The thermal analysis data clearly demonstrates that, the application of ultrasound to spray dried particles modifies the physical characteristics of the particles. With respect to this analyses the mass loss for the ultrasound treated material was only 0.018% compared with the initial; spray dried material which was 1.042%. The loss can be attributed to both residual acetone solvent and any water present, in turn derived from the hygroscopic nature of the first spray dried particles. For spray dried material not subjected to ultrasonic treatment, in FIG. 13, the exotherm, that is the positive peak on the solid line at 93.38° C. is indicative of amorphous to crystalline transformation in the DSC apparatus. For the particles prepared as described in this invention there was no exotherm noted in FIG. 13 in the broken line. This phenomenon is indicative of crystalline product being present in the particles of the invention. There was definite improvement in crystalline characteristic of processed material. In addition, the SEM images, FIGS. 10 and 11, shows clear difference in morphology before and after ultrasonic treatment.

Differential Scanning Calorimetry

DSC experiments were performed with a DSC Q2000 V24.2 build 107 (TA Instruments, UK). Approximately 3 mg of material was weighed into the sample pan of the DSC and subjected to heating ramp of 100° C./min add heated to 275° C. The DSC measurements were carried out using the following protocols.

Spray dried material not treated with ultrasound according to the present invention
  Instrument DSC Q2000 V24.2 Build 107
  Module DSC Standard Cell RC
  Sample px02-262-spray dried
  Size 2.140 mg
  Method Fast Heating expt 100° C.-min
  Weighed sample is heated at rate of 100° C./Min to 275° C.
Material treated with ultrasound according to the process of the present invention
  Instrument DSC Q2000 V24.2 Build 107
  Module DSC Standard Cell RC
  Sample px02-262-post ultrasound
  Size 3.590 mg
  Method Fast Heating expt 100° C.-Min
  Weighed sample is heated at rate of 100° C./Min to 275° C.

Thermogravimetric Analysis

TGA experiments were performed with a TGA Q50 V20.10 Build 36 (TA Instruments, UK). Approximately 3-4 mg of material was weighed into the sample pan of the TGA and subjected to heating ramp of 25° C./min and heated to 300° C. The TGA measurements were carried out using the following protocols:

Spray dried material was not treated with ultrasound according to the present invention
  Instrument TGA Q50 V20.10 Build 36
  Module TGA
  Sample PLXB017-63-A1
  Size 3.173 mg
  Method heating experiment 25° C.-min
  Weighed sample is heated at rate of 25° C./Min to 300° C.
Material treated with ultrasound according to the process of the present invention
  instrument TGA Q50 V20.10 Build 36
  Module TGA
  Sample PLXB017-63-U1
  Size 4.983 mg
  Method heating experiment 25° C.-min
  Weighed sample is heated at rate of 25° C./Min to 300° C.

The invention claimed is:
1. A process for increasing the crystallinity of at least one solid material which is less than 100% crystalline and containing residual solvent, comprising applying ultrasound to the solid material, wherein the solid material is selected from the group consisting of an active pharmaceutical agent, a pharmaceutical excipient, and mixtures of two or more thereof, thereby increasing the crystallinity of said solid material.

2. A process according to claim 1, wherein the solid material is a particulate solid material having a mass median aerodynamic diameter of up to 10 μm.

3. A process according to claim 1, wherein the solid material is obtained from a process selected from the group consisting of mechanical micronization, milling, jet milling, grinding, rapid precipitation, freeze drying, lyophilisation, and rapid expansion of supercritical solutions.

4. A process according to claim 1, wherein prior to the application of said process, the solid material is less than 50% crystalline.

5. A process according to claim 1, wherein the solid material contains less than 2% by weight of the solvent.

6. A process according to claim 1, wherein the process comprises:
  (i) forming a solution of at least one solid material in a solvent;
  (ii) subjecting the solution to a process selected from the group consisting of rapid precipitation, freeze drying, lyophilisation, rapid expansion of supercritical solutions, spray drying or mixtures thereof, wherein the said dissolved solid material containing residual solvent is converted into to a solid material; and
  (iii) applying ultrasound to said solid material containing residual solvent from step (ii).

7. A process according to claim 1, wherein the process is sequential, and step (iii) takes place immediately after step (ii).

8. A process according to claim 1, wherein the process comprises:
  (a) subjecting at least one solid material to mechanical micronization, milling, jet milling, grinding or mixtures thereof; and
  (b) applying ultrasound to the solid material from step (a).

9. A process according to claim 6 or claim 8 wherein step (iii) or step (b) further comprises applying microwave energy to the solid material from step (ii) or (a).

10. A process according to claim 1, wherein the solid material is a pharmaceutically active ingredient selected from the group consisting of anti-allergics, bronchodilators, anti-inflammatory steroids and mixtures thereof.

11. A process according to claim 1, wherein the solid material is a pharmaceutical ingredient selected from the group consisting of fluticasone, budesonide, cromoglycate, salbutamol, salmeterol, terbutaline, reproterol, beclomethasone dipropionate, (−)-4-amino-3,5-dichloro-α-[[[6-[2-(2-pyridinyl)ethoxy]hexyl]amino]-methyl]benzenemethanol, glycopyrronium bromide, darotropium, aclidinium, tiotropium, theophylline, arofylline, zarfirlukast, monterlukast, carmoterol, formoterol, or indacaterol and physiologically acceptable salts and solvates thereof.

12. A process according to claim 1, wherein the solid material comprises at least one pharmaceutically active ingredient and a carrier substance.

13. A process according to claim 1, wherein the solid material does not comprise a non-solvent.

14. A process according to claim 1, wherein the ultrasound is applied by means of an ultrasonic vibrating sieve, an ultrasonic vibrating conveyor belt or an ultrasonic resonating chamber.

* * * * *